US006875588B2

(12) United States Patent
Harvey et al.

(10) Patent No.: US 6,875,588 B2
(45) Date of Patent: Apr. 5, 2005

(54) OVOMUCOID PROMOTER AND METHODS OF USE

(75) Inventors: Alex J. Harvey, Athens, GA (US); Youliang Wang, Athens, GA (US)

(73) Assignee: AviGenics, Inc., Athens, GA (US)

( * ) Notice: Subject to any disclaimer, the term of this patent is extended or adjusted under 35 U.S.C. 154(b) by 5 days.

(21) Appl. No.: 09/998,716

(22) Filed: Nov. 30, 2001

(65) Prior Publication Data

US 2003/0126628 A1 Jul. 3, 2003

(51) Int. Cl.[7] .................. C12P 21/06; C07H 21/04; C12N 15/85; C12N 5/00
(52) U.S. Cl. ............... 435/69.51; 435/69.1; 435/320.1; 435/325; 435/349; 536/24.1
(58) Field of Search .................... 435/320.1, 325, 435/349, 69.1, 69.51; 536/24.1

(56) References Cited

U.S. PATENT DOCUMENTS

| | | | |
|---|---|---|---|
| 4,237,224 A | 12/1980 | Cohen et al. | 435/69.1 |
| 4,603,112 A | 7/1986 | Paoletti et al. | 435/235.1 |
| 4,722,848 A | 2/1988 | Paoletti et al. | 424/199.1 |
| 4,769,330 A | 9/1988 | Paoletti et al. | 435/463 |
| 5,174,993 A | 12/1992 | Paoletti et al. | 424/199.1 |
| 5,175,384 A | 12/1992 | Krimpenfort et al. | 800/11 |
| 5,338,683 A | 8/1994 | Paoletti et al. | 435/235.1 |
| 5,494,807 A | 2/1996 | Paoletti et al. | 435/69.3 |
| 5,505,941 A | 4/1996 | Paoletti et al. | 424/93.2 |
| 5,580,859 A | 12/1996 | Felgner et al. | 514/44 |
| 5,589,466 A | 12/1996 | Felgner et al. | 514/44 |
| 5,591,639 A | 1/1997 | Bebbington | 435/320.1 |

FOREIGN PATENT DOCUMENTS

| | | |
|---|---|---|
| WO | WO 92/06180 | 10/1990 |
| WO | WO 92/19749 | 5/1991 |
| WO | WO 92/20316 | 5/1991 |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |

OTHER PUBLICATIONS

Entrez Nucleotide Database entry Accession No. M16141 (published 1994).*
Arnone et al. The hardwiring of development: organization and function of genomic regulatory systems. Development. May 1997;124(10):1851–64.*

Molecular Structure and Flanking Nucleotide Sequences of the Natural Chicken Ovomucoid Gene,Lai et al; Cell 18:829–842 (Nov. 1979).

DNA methylation: organ specific variations in the methylation pattern within and around ovalbumin and other chicken genes, Mandel et al; Nucleic Acids Research 7:2081–2103(1979).

Ovoinhibitor Introns Specify Functional Domains as in the Related and Linked Ovomucoid Gene*, Scott et al; Journal of Biol. Chemistry, 262:5899–5907(1987).

Deoxyribonuclease I Sensitivity of the Ovomucoid–Ovoinhibitor Gene Complex in Oviduct Nuclei and Relative Location of CR1 Repetitive Sequences, Scott et al; Biochemistry 26:6831–6840 (1987).

Isolation and characterization of the chicken ovomucoid gene, Lindenmaier et al; Nucleic Acids Research, 7:1221–1232 (1979).

The chick ovomucoid gene contains at least six intervening sequences, Catterall et al; Nature 278: 323–327 (Mar. 1979).

Effect of Estrogen on Gene Expression In the Chick Oviduct. Regulation of the Ovomucoid Gene, Tsai et al; Biochemistry 17:5773–5780 (1978).

Identification of potential ovomucoid mRNA precursors in chick oviduct nuclei, Nordstrom et al; Nature 278:328–331 (Mar. 1979).

mRNA Complexity and Egg White Protein mRNA Content in Mature and Hormone–Withdrawn Oviduct, Hynes et al; Cell 11:923–932 (Aug. 1977).

* cited by examiner

*Primary Examiner*—David Guzo
*Assistant Examiner*—Daniel M. Sullivan
(74) *Attorney, Agent, or Firm*—Kyle D. Yesland

(57) ABSTRACT

The present invention provides novel isolated nucleic acids comprising an avian nucleic acid sequence encoding an ovomucoid gene expression control region. The ovomucoid promoter region of the present invention allows expression of an operably linked heterologous nucleic acid insert in a transfected cell such as, for example, an avian oviduct cell. The isolated avian ovomucoid promoter of the present invention may be operably linked with a selected nucleic acid insert, wherein the nucleic acid insert encodes a polypeptide desired to be expressed in a transfected cell. The recombinant DNA of the present invention may further comprise a polyadenylation signal sequence. The present invention further includes expression vectors comprising an isolated avian ovomucoid gene expression control region of the present invention, and transfected cells and transgenic avians comprising the expression vectors.

37 Claims, 7 Drawing Sheets

| | | |
|---|---|---|
| OVINs1: | GGGAAACAATCTGCCTTGCA | SEQ ID NO: 3 |
| OVINs2: | TAGGCAGAGCAATAGGACTCTCAACCTCGT | SEQ ID NO: 1 |
| OVINs4: | AGATGAGGTGGATGGTTTAC | SEQ ID NO: 7 |
| OVINs5: | CAGCTTCTGCTAGCGTAGGT | SEQ ID NO: 8 |
| OVINs6: | ACGTGAACTCAAAGAGGCAC | SEQ ID NO: 9 |
| OVINs7: | ATCTCCTGAGCTCGGTGCTT | SEQ ID NO: 10 |
| OVINs8: | ACGAGGTTCCATGTCTTTCA | SEQ ID NO: 11 |
| OVMUa1: | AAGCCACAAAGCACGAAAGAG | SEQ ID NO: 4 |
| OVMUa2: | AAGCTTCTGCAGCACTCTGGGAGTTACTCA | SEQ ID NO: 2 |
| OVMUa3: | TAAATAGCACAGAACGCTGAGGGGAGTAAGG | SEQ ID NO: 12 |
| OVMUa4: | GAAGAGCTTGGTAGAAGACT | SEQ ID NO: 13 |
| OVMUa5: | ATGGAAATATGGGTTTCCTTC | SEQ ID NO: 14 |
| OVMUa6: | GCAGCTTATGGCTAATCGCT | SEQ ID NO: 15 |
| OVMUa7: | AGTGACCACTATCTGACCTG | SEQ ID NO: 16 |
| OVMUa8: | TAATCAGGAAGGCACACAGC | SEQ ID NO: 17 |
| OVMUP4.7.1: | AGATCTGGAGCAGCACTTGT | SEQ ID NO: 18 |
| OVMUP4.7.2: | AGCATGAAGTTCCTCACCCA | SEQ ID NO: 19 |
| OVMUP4.7.3: | ATGGAGAGGAATATTCCCTT | SEQ ID NO: 20 |
| OVMUP4.7.4: | ATTTCTCCAGGCGTGTGG | SEQ ID NO: 21 |
| OVMUP5.5.1: | ATTTCTCCAGGCGTGTGG | SEQ ID NO: 22 |
| OVMUP5.5.2: | ATGCGAGTGAAGGAGAGTTC | SEQ ID NO: 23 |
| OVMUP5.5.3: | GCAGCACGTGTAAGCTTGTA | SEQ ID NO: 24 |
| OVMUP5.5.4: | CAAGGCAAATTATCAGCAGA | SEQ ID NO: 25 |
| OVMUa9: | AAATGAAGCCGGCTGTTTC | SEQ ID NO: 27 |
| OVINs9 | CTCTCAGCCACTCTGAACAA | SEQ ID NO: 28 |

Fig. 3

```
TAGGCAGAGCAATAGGACTCTCAACCTCGTGAGTATGGCAGCATGTTAACTCTGCACTGG    60
                OVOINHIBITOR 3' UNTRANSLATED REGION
AGTCCAGCGTGGGAAACAATCTGCCTTGCACATGAGTCTTCGTGGGCCAATATTCCCCAA
                OVOINHIBITOR 3' UNTRANSLATED REGION
CGGTTTTCCTTCAGCTTGTCTTGTCTCCTAAGCTCTCAAAACACCTTTTTGGTGAATAAA
                OVOINHIBITOR 3' UNTRANSLATED REGION
CTCACTTGGCAACGTTTATCTGTCTTACCTTAGTGTCACGTTTCATCCCTATTCCCCTTT

CTCCTCCTCCGTGTGGTACACAGTGGTGCACACTGGTTCTTCTGTTGATGTTCTGCTCTG   300
ACAGCCAATGTGGGTAAAGTTCTTCCTGCCACGTGTCTGTGTTGTTTTCACTTCAAAAAG
GGCCCTGGGCTCCCCTTGGAGCTCTCAGGCATTTCCTTAATCATCACAGTCACGCTGGCA
GGATTAGTCCCTCCTAAACCTTAGAATGACCTGAACGTGTGCTCCCTCTTTGTAGTCAGT
GCAGGGAGACGTTTGCCTCAAGATCAGGGTCCATCTCACCCACAGGGCCATTCCCAAGAT
GAGGTGGATGGTTTACTCTCACAAAAAGTTTTCTTATGTTTGGCTAGAAAGGAGAACTCA   600
CTGCCTACCTGTGAATTCCCCTAGTCCTGGTTCTGCTGCCACTGCTGCCTGTGCAGCCTG
TCCCATGGAGGGGGCAGCAACTGCTGTCACAAAGGTGATCCCACCCTGTCTCCACTGAAA
TGACCTCAGTGCCACGTGTTGTATAGGGTATAAAGTACGGGAGGGGGATGCCCGGCTCCC
TTCAGGGTTGCAGAGCAGAAGTGTCTGTGTATAGAGTGTGTCTTAATCTATTAATGTAAC
AGAACAACTTCAGTCCTAGTGTTTTGTGGGCTGGAATTGCCCATGTGGTAGGGACAGGCC   900
TGCTAAATCACTGCAATCGCCTATGTTCTGAAGGTATTTGGGAAAGAAAGGGATTTGGGG
GATTGCCTGTGATTGGCTTTAATTGAATGGCAAATCACAGGAAAGCAGTTCTGCTCAACA
GTTGGTTGTTTCAGCCAATTCTTGCAGCCAAAGAGCCGGGTGCCCAGCGATATAATAGTT
GTCACTTGTGTCTGTATGGATGACAGGGAGGTAGGGTGACCTGAGGACCACCCTCCAGCT
TCTGCTAGCGTAGGTACAGTCACCACCTCCAGCTCCACACGAGTCCCATCGTGGTTTACC  1200
AAAGAAACACAATTATTTGGACCAGTTTGGAAAGTCACCCGCTGAATTGTGAGGCTAGAT
TAATAGAGCTGAAGAGCAAATGTTCCCAACTTGGAGATACTAGTTGGTATTAGTATCAGA
GGAACAGGGCCATAGCACCTCCATGCTATTAGATTCCGGCTGGCATGTACTTTTCAAGAT
GATTTGTAACTAACAATGGCTTATTGTGCTTGTCTTAAGTCTGTGTCCTAATGTAAATGT
TCCTTTGGTTTATATAACCTTCTTGCCATTTGCTCTTCAGGTGTTCTTGCAGAACACTGG  1500
CTGCTTTAATCTAGTTTAACTGTTGCTTGATTATTCTTAGGGATAAGATCTGAATAAACT
TTTTGTGGCTTTGGCAGACTTTAGCTTGGGCTTAGCTCCCACATTAGCTTTTGCTGCCTT
TTCTGTGAAGCTATCAAGATCCTACTCAATGACATTAGCTGGGTGCAGGTGTACCAAATC
CTGCTCTGTGGAACACATTGTCTGATGATACCGAAGGCAAACGTGAACTCAAAGAGGCAC
AGAGTTAAGAAGAAGTCTGTGCAATTCAGAGGAAAAGCCAAAGTGGCCATTAGACACACT  1800
TTCCATGCAGCATTTGCCAGTAGGTTTCATATAAAACTACAAAATGGAATAAACCACTAC
AAATGGGAAAAGCCTGATACTAGAATTTAAATATTCACCCAGGCTCAAGGGGTGTTTCAT
GGAGTAATATCACTCTATAAAAGTAGGGCAGCCAATTATTCACAGACAAAGCTTTTTTTT
TTCTGTGCTGCAGTGCTGTTTTTCGGCTGATCCAGGGTTACTTATTGTGGGTCTGAGAGC
TGAATGATTTCTCCTTGTGTCATGTTGGTGAAGGAGATATGGCCAGGGGGAGATGAGCAT  2100
GTTCAAGAGGAAACGTTGCATTTTGGTGGCTTGGGAGAAAGGTAGAACGATATCAGGTCC
ATAGTGTCACTAAGAGATCTGAAGGATGGTTTTACAGAACAGTTGACTTGGCTGGGTGCA
GGCTTGGCTGTAAATGGATGGAAGGATGGACAGATGGGTGGACAGAGATTTCTGTGCAGG
AGATCATCTCCTGAGCTCGGTGCTTGACAGACTGCAGATCCATCCCATAACCTTCTCCAG
CATGAGAGCGCGGGGAGCTTTGGTACTGTTCAGTCTGCTGCTTGTTGCTTCCTGGGTGCA  2400
CAGTGGTGATTTTCTTACTCACACAGGGCAAAAACCTGAGCAGCTTCAAAGTGAACAGGT
TGCTCTCATAGGCCATTCAGTTGTCAAGATGAGGTTTTTGGTTTCTTGTTTTGTAAGGTG
GGAAGAAGCACTGAAGGATCAGTTGCGAGGGCAGGGGTTTAGCACTGTTCAGAGAAGTCT
TATTTTAACTCCTCTCATGAACAAAAAGAGATGCAGGTGCAGATTCTGGCAAGCATGCAG
TGAAGGAGAAAGCCCTGAATTTCTGATATATGTGCAATGTTGGGCACCTAACATTCCCCG  2700
CTGAAGCACAGCAGCTCCAGCTCCATGCAGTACTCACAGCTGGTGCAGCCCTCGGCTCCA
GGGTCTGAGCAGTGCTGGGACTCACGAGGTTCCATGTCTTTCACACTGATAATGGTCCAA
                                                              CR1
TTTCTGGAATGGGTGCCCATCCTTGGAGGTCCCCAAGGCCAGGCTGGCTGCGTCTCCGAG
                              CR1
CAGCCCGATCTGGTGGTGAGTAGCCAGCCCATGGCAGGAGTTAGAGCCTGATGGTCTTTA
                              CR1
```

FIG. 4A

```
AGGTCCCTTCCAACCTAAGCCATCCTACGATTCTAGGAATCATGACTTGTGAGTGTGTAT 3000
                              CR1
TGCAGAGGCAATATTTTAAAGTTATAAATGTTTTCTCCCCTTCCTTGTTTGTCAAAGTTA
      CR1
TCTTGATCGCCTTATCAATGCTTTTGGAGTCTCCAGTCATTTTTCTTACAMCAAAAAGAG
GAGGAAGAATGAAGAGAATCATTTAATTTCTTGATTGAATAGTAGGATTCAGAAAGCTGT
ACGTAATGCCGTCTCTTTGTATCGAGCTGTAAGGTTTCTCATCATTTATCAGCGTGGTAC
ATATCAGCACTTTTCCATCTGATGTGGAAAAAAAAATCCTTATCATCTACAGTCTCTGTA 3300
CCTAAACATCGCTCAGACTCTTTACCAAAAAGCTATAGGTTTTAAAACTACATCTGCTG
ATAATTTGCCTTGTTTAGCTCTTCTTCCATATGCTGCGTTTGTGAGAGGTGCGTGGATG
GGCCTAAACTCTCAGCTGCTGAGCTTGATGGGTGCTTAAGAATGAAGCACTCACTGCTGA
AACTGTTTTCATTTCACAGGAATGTTTTAGTGGCATTGTTTTTATAACTACATATTCCTC
AGATAAATGAAATCCAGAAATAATTATGCAAACTCACTGCATCCGTTGCACAGGTCTTTA 3600
TCTGCTAGCAAAGGAAATAATTTGGGGATGGCAAAAACATTCCTTCAGACATCTATATTT
AAAGGAATATAATCCTGGTACCCACCCACTTCATCCCTCATTATGTTCACACTCAGAGAT
ACTCATTCTCTTGTTGTTATCATTTGATAGCGTTTTCTTTGGTTCTTTGCCACGCTCTGG
GCTATGGCTGCACGCTCTGCACTGATCAGCAAGTAGATGCGAGGGAAGCAGCAGTGAGAG
GGGCTGCCCTCAGCTGGCACCCAGCCGCTCAGCCTAGGAGGGGACCTTGCCTTTCCACCA 3900
GCTGAGGTGCAGCCCTACAAGCTTACACGTGCTGCGAGCAGGTGAGCAAAGGGAGTCTTC
ATGGTGTGTTTCTTGCTGCCCGGAAGCAAAACTTTACTTTCATTCATTCCCCTTGAAGAA
TGAGGAATGTTTGGAAACGGACTGCTTTACGTTCAATTTCTCTCTTCCCTTTAAGGCTCA
GCCAGGGGCCATTGCTGAGGACGGCATCGGGGCCCCCTGGACCAAATCTGTGGCACAGAT
GGTTTCACTTACATCAGTGGATGTGGGATCTGCGCCTGTAATGTGTCCTTCTGAAGGAAG 4200
GAACGTGCCTTCCAAGTGCCAGCCCCACAGCCCCCAGCCCCTCCCTGTGCTGCTCCAATT
CATCTCCTCTTCCTCCTTCTCCCTTTGCTGTTTGTGCTCGGGTAGAAATCATGAAGATTT
AGAAGAGAAAACAAAATAACTGGAGTGGAAACCCAGGTGATGCAGTTCATTCAGCTGTCA
TAGGTTTGTCGTTGCTATAGGTCTGTATCAGAGATGCTARCACCACTTTGCTGTCGGTGC
TTAACTCGGGTGAACTCTCCTTCACTCGCATCATTTGCGGGCCTTATTTACATCCCCAGC 4500
ATCCATCACCCTCTGGGAAAATGGGCGCACTGGATCTCTAATGGAAGACTTTCCCTCTTT
CAGAGCCTGTGGGATGTGCAGTGACAAGAAACGTGGAGGGGCTGAGCAGCAGCACTGCCC
CCAGGGAGCAGGAGCGGATGCCATCGGTGGCAGCATCCCAAATGATGTCAGCGGATGCTG
AGCAGGCAGCGGACGAACGGACAGAAGCGATGCGTACACCTTCTGTTGACATGGTATTTG
GCAGCGATTTAACACTCGCTTCCTAGTCCTGCTATTCTCCACAGGCTGCATTCAAATGAA 4800
CGAAGGGAAGGGAGGCAAAAAGATGCAAAATCCGAGACAAGCAGCAGAAATATTTCTTCG
CTACGGAAGCGTGCGCAAACAACCTTCTCCAACAGCACCAGAAGAGCACAGCGTAACCTT
TTTCAAGACCAGAAAAGGAAATTCACAAAGCCTCTGTGGATACCAGCGCGTTCAGCTCTC
CTGATAGCAGATTTCTTGTCAGGTTGCGAATGGGGTATGGTGCCAGGAGGTGCAGGGACC
ATATGATCATATACAGCACAGCAGTCATTGTGCATGTATTAATATATATTGAGTAGCAGT 5100
GTTACTTTGCCAAAGCAATAGTTCAGAGATGAGTCCTGCTGCATACCTCTATCTTAAAAC
TAACTTATAAATAGTAAAACCTTCTCAGTTCAGCCACGTGCTCCTCTCTGTCAGCACCAA
TGGTGCTTCGCCTGCACCCAGCTGCAAGGAATCAGCCCGTGATCTCATTAACACTCAGCT
CTGCAGGATAAATTAGATTGTTCCACTCTCTTTTGTTGTTAATTACGACGGAACAATTGT
TCAGTGCTGATGGTCCTAATTGTCAGCTACAGAAAACGTCTCCATGCAGTTCCTTCTGCG 5400
CCAGCAAACTGTCCAGGCTATAGCACCGTGATGCATGCTACCTCTCACTCCATCCTTCTT
CTCTTTCCCACCAGGGAGAGCTGTGTGTTTTCACTCTCAGCCACTCTGAACAATACCAAA
CTGCTACGCACTGCCTCCCTCGGAAAGAGAATCCCCTTGTTGCTTTTTTATTTACAGGAT
CCTTCTTAAAAAGCAGACCATCATTCACTGCAAACCCAGAGCTTCATGCCTCTCCTTCCA
CAACCGAAAACAGCCGGCTTCATTTGTCTTTTTTAAATGCTGTTTTCCAGGTGAATTTTG 5700
GCCAGCGTGTTGGCTGAGATCCAGGAGCACGTGTCAGCTTTCTGCTCTCATTGCTCCTGT
TCTGCATTGCCTCTTTCTGGGGTTTCCAAGAGGGGGGGAGACTTTGCGCGGGATGAGAT
AATGCCCCTTTTCTTAGGGTGGCTGCTGGGCAGCAGAGTGGCTCTGGGTCACTGTGGCAC
CAATGGGAGGCACCAGTGGGGGTGTGTTTTGTGCAGGGGGGAAGCATTCACAGAATGGGG
CTGATCCTGAAGCTTGCAGTCCAAGGCTTTGTCTGTGTACCCAGTGAAATCCTTCCTCTG 6000
TTACATAAAGCCCAGATAGGACTCAGAAATGTAGTCATTCCAGCCCCCTCTTCCTCAGA
TCTGGAGCAGCACTTGTTTGCAGCCAGTCCTCCCCAAAATGCACAGACCTCGCCGAGTGG
AGGGAGATGTAAACAGCGAAGGTTAATTACCTCCTTGTCAAAAACACTTTGTGGTCCATA
```

FIG. 4B

```
GATGTTTCTGTCAATCTTACAAAACAGAACCGAGAGGCAGCGAGCACTGAAGAGCGTGTT
CCCATGCTGAGTTAATGAGACTTGGCAGCTCGCTGTGCAGAGATGATCCCTGTGCTTCAT 6300
GGGAGGCTGTAACCTGTCTCCCCATCGCCTTCACACCGCAGTGCTGTCCTGGACACCTCA
CCCTCCATAAGCTGTAGGATGCAGCTGCCCAGGGATCAAGAGACTTTTCCTAAGGCTCTT
AGGACTCATCTTTGCCGCTCAGTAGCGTGCAGCAATTACTCATCCCAACTATACTGAATG
GGTTTCTGCCAGCTCTGCTTGTTTGTCAATAAGCATTTCTTCATTTTGCCTCTAAGTTTC
TCTCAGCAGCACCGCTCTGGGTGACCTGAGTGGCCACCTGGAACCCGAGGGGCACAGCCA 6600
CCACCTCCCTGTTGCTGCTGCTCCAGGGACTCATGTGCTGCTGGATGGGGGAAGCATGA
AGTTCCTCACCCAGACACCTGGGTTGCAATGGCTGCAGCGTGCTCTTCTTGGTATGCAGA
TTGTTTCCAGCCATTACTTGTAGAAATGTGCTGTGGAAGCCCTTTGTATCTCTTTCTGTG
GCCCTTCAGCAAAAGCTGTGGGAAAGCTCTGAGGCTGCTTTCTTGGGTCGTGGAGGAATT
GTATGTTCCTTCTTTAACAAAAATTATCCTTAGGAGAGAGCACTGTGCAAGCATTGTGCA 6900
CATAAAACAATTCAGGTTGAAAGGGCTCTCTGGAGGTTTCCAGCCTGACTACTGCTCGAA
GCAAGGCCAGGTTCAAAGATGGCTCAGGATGCTGTGTGCCTTCCTGATTATCTGTGCCAC
CAATGGAGGAGATTCACAGCCACTCTGCTTCCCGTGCCACTCATGGAGAGGAATATTCCC
TTATATTCAGATAGAATGTTATCCTTTAGCTCAGCCTTCCCTATAACCCCATGAGGGAGC
TGCAGATCCCCATACTCTCCCCTTCTCTGGGGTGAAGGCCGTGTCCCCAGCCCCCCTTC 7200
CCACCCTGTGCCCTAAGCAGCCCGCTGGCCTCTGCTGGATGTGTGCCTATATGTCAATGC
CTGTCCTTGCAGTCCAGCCTGGGACATTTAATTCATCACCAGGGTAATGTGGAACTGTGT
CATCTTCCCCTGCAGGGTACAAAGTTCTGCACGGGGTCCTTTCGGTTCAGGAAAACCTTC
ACTGGTGCTACCTGAATCAAGCTCTATTTAATAAGTTCATAAGCACATGGATGTGTTTTC
CTAGAGATACGTTTTAATGGTATCAGTGATTTTTATTTGCTTTGTTGCTTACTTCAAACA 7500
GTGCCTTTGGGCAGGAGGTGAGGGACGGGTCTGCCGTTGGCTCTGCAGTGATTTCTCCAG
GCGTGTGGCTCAGGTCAGATAGTGGTCACTCTGTGGCCAGAAGAAGGACAAAGATGGAAA
TTGCAGATTGAGTCACGTTAAGCAGGCATCTTGGAGTGATTTGAGGCAGTTTCATGAAAG
AGCTACGACCACTTATTGTTGTTTTCCCCTTTTACAACAGAAGTTTTCATCAAAATAACG
TGGCAAAGCCCAGGAATGTTTGGGAAAGTGTAGTTAAATGTTTTGTAATTCATTTGTCG 7800
GAGTGCTACCAGCTAAGAAAAAAGTCCTACCTTTGGTATGGTAGTCCTGCAGAGAATACA
ACATCAATATTAGTTTGGAAAAAAACACCACCACCACCAGAAACTGTAATGGAAAATGTA
AACCAAGAAATTCCTTGGGTAAGAGAGAAAGGATGTCGTATACTGGCCAAGTCCTGCCCA
GCTGTCAGCCTGCTGACCCTCTGCAGTTCAGGACCATGAAACGTGGCACTGTAAGACGTG
TCCCCTGCCTTTGCTTGCCCACAGATCTCTGCCCTTGTGCTGACTCCTGCACACAAGAGC 8100
ATTCCCTGTAGCCAAACAGCGATTAGCCATAAGCTGCACCTGACTTTGAGGATTAAGAG
TTTGCAATTAAGTGGATTGCAGCAGGAGATCAGTGGCAGGGTTGCAGATGAAATCCTTTT
CTAGGGGTAGCTAAGGGCTGAGCAACCTGTCCTACAGCACAAGCCAAACCAGCCAAGGGT
TTTCCTGTGCTGTTCACAGAGGCAGGGCCAGCTGGAGCTGGAGGAGGTTGTGCTGGGACC
CTTCTCCCTGTGCTGAGAATGGAGTGATTTCTGGGTGCTGTTCCTGTGGCTTGCACTGAG 8400
CAGCTCAAGGGAGATCGGTGCTCCTCATGCAGTGCCAAAACTCGTGTTTGATGCAGAAAG
ATGGATGTGCACCTCCCTCCTGCTAATGCAGCCGTGAGCTTATGAAGGCAATGAGCCCTC
AGTGCAGCAGGAGCTGTAGTGCACTCCTGTAGGTGCTAGGGAAAATCTCTGGTTCCCAGG
GATGCATTCATAAGGGCAATATATCTTGAGGCTGCGCCAAATCTTTCTGAAATATTCATG
CGTGTTCCCTTAATTTATAGAAACAAACACAGCAGAATAATTATTCCAATGCCTCCCCTC 8700
GAAGGAAACCCATATTTCCATGTAGAAATGTAACCTATATACACACAGCCATGCTGCATC
CTTCAGAACGTGCCAGTGCTCATCTCCCATGGCAAAATACTACAGGTATTCTCACTATGT
TGGACCTGTGAAAGGAACCATGGTAAGAAACTTCGGTTAAAGGTATGGCTGCAAAACTAC
TCATACCAAAACAGCAGAGCTCCAGACCTCCTCTTAGGAAAGAGCCACTTGGAGAGGGAT
GGTGTGAAGGCTGGAGGTGAGAGACAGAGCCTGTCCCAGTTTTCCTGTCTCTATTTTCTG 9000
AAACGTTTGCAGGAGGAAAGGACAACTGTACTTTCAGGCATAGCTGGTGCCCTCACGTAA
ATAAGTTCCCCGAACTTCTGTGTCATTTGTTCTTAAGATGCTTTGGCAGAACACTTTGAG
TCAATTCGCTTAACTGTGACTAGGTCTGTAAATAAGTGCTCCCTGCTGATAAGGTTCAAG
TGACATTTTTAGTGGTATTTGACAGCATTTACCTTGCTTTCAAGTCTTCTACCAAGCTCT
TCTATACTTAAGCAGTGAAACCGCCAAGAAACCCTTCCTTTTATCAAGCTAGTGCTAAAT 9300
ACCATTAACTTCATAGGTTAGATACGGTGCTGCCAGCTTCACCTGGCAGTGGTTGGTCAG
TTCTGCTGGTGACAAAGCCTCCCTGGCCTGTGCTTTTACCTAGAGGTGAATATCCAAGAA
TGCAGAACTGCATGGAAAGCAGAGCTGCAGGCACGATGGTGCTGAGCCTTAGCTGCTTCC
TGCTGGGAGATGTGGATGCAGAGACGAATGAAGGACCTGTCCCTTACTCCCCTCAGCATT
```

FIG. 4C

CTGTGCTATTTAGGGTTCTACCAGAGTCCTTAAGAGGTTTTTTTTTTTTTGGTCCAAAA 9600
GTCTGTTTGTTTGGTTTTGACCACTGAGAGCATGTGACACTTGTCTCAAGCTATTAACCA
AGTGTCCAGCCAAAATCAATTGCCTGGGAGACGCAGACCATTACCTGGAGGTCAGGACCT
CAATAAATATTACCAGCCTCATTGTGCCGCTGACAGATTCAGCTGGCTGCTCCGTGTTCC
AGTCCAACAGTTCGGACGCCACGTTTGTATATATTTGCAGGCAGCCTCGGGGGGACCATC
TCAGGAGCAGAGCACCGGCAGCCGCCTGCAGAGCCGGGCAGTACCTCACCATGGCCATGG 9900
<u>     OVOMUCOID 5' UNTRANSLATED REGION                         </u>
CAGGTGTCTTCGTGCTGTTCTCTTTCGTGCTTTGTGGCTTCCTCCCAGGTGAGTAACTCC
<u>                OVOMUCOID CODING REGION                        </u>
CAGAGTGCTGCAGAAGCTT 9979

FIG. 4D

SEQUENCE LISTING

<160> NUMBER OF SEQ ID NOS: 28

<210> SEQ ID NO 1
<211> LENGTH: 30
<212> TYPE: DNA
<213> ORGANISM: Artificial Sequence
<220> FEATURE:
<223> OTHER INFORMATION: Primer OVINs2

<400> SEQUENCE: 1
taggcagagc aataggactc tcaacctcgt                                30

<210> SEQ ID NO 2
<211> LENGTH: 30
<212> TYPE: DNA
<213> ORGANISM: Artificial Sequence
<220> FEATURE:
<223> OTHER INFORMATION: Primer OVMa2

<400> SEQUENCE: 2
aagcttctgc agcactctgg gagttactca             30

<210> SEQ ID NO 3
<211> LENGTH: 20
<212> TYPE: DNA
<213> ORGANISM: Artificial Sequence
<220> FEATURE:
<223> OTHER INFORMATION: Primer OVINs1

<400> SEQUENCE: 3
gggaaacaat ctgccttgca             20

<210> SEQ ID NO 4
<211> LENGTH: 21
<212> TYPE: DNA
<213> ORGANISM: Artificial Sequence
<220> FEATURE:
<223> OTHER INFORMATION: Primer OVMUa1

<400> SEQUENCE: 4
aagccacaaa gcacgaaaga g             21

<210> SEQ ID NO 5
<211> LENGTH: 20
<212> TYPE: DNA
<213> ORGANISM: Artificial Sequence
<220> FEATURE:
<223> OTHER INFORMATION: Primer T3

<400> SEQUENCE: 5
taatacgact cactataggg             20

<210> SEQ ID NO 6
<211> LENGTH: 20
<212> TYPE: DNA
<213> ORGANISM: Artificial Sequence
<220> FEATURE:
<223> OTHER INFORMATION: Primer T7

<400> SEQUENCE: 6
attaaccctc actaaggga             20

<210> SEQ ID NO 7
<211> LENGTH: 20
<212> TYPE: DNA
<213> ORGANISM: Artificial Sequence
<220> FEATURE:
<223> OTHER INFORMATION: Primer OVINs4

<400> SEQUENCE: 7
agatgaggtg gatggtttac             20

<210> SEQ ID NO 8
<211> LENGTH: 20
<212> TYPE: DNA
<213> ORGANISM: Artificial Sequence
<220> FEATURE:

-continued

```
<223> OTHER INFORMATION: Primer OVINs5

<400> SEQUENCE: 8
cagcttctgc tagcgtaggt                                              20

<210> SEQ ID NO 9
<211> LENGTH: 20
<212> TYPE: DNA
<213> ORGANISM: Artificial Sequence
<220> FEATURE:
<223> OTHER INFORMATION: Primer OVINs6

<400> SEQUENCE: 9
acgtgaactc aaagaggcac                                              20

<210> SEQ ID NO 10
<211> LENGTH: 20
<212> TYPE: DNA
<213> ORGANISM: Artificial Sequence
<220> FEATURE:
<223> OTHER INFORMATION: Primer OVINs7

<400> SEQUENCE: 10
atctcctgag ctcggtgctt                                              20

<210> SEQ ID NO 11
<211> LENGTH: 20
<212> TYPE: DNA
<213> ORGANISM: Artificial Sequence
<220> FEATURE:
<223> OTHER INFORMATION: Primer OVINs8

<400> SEQUENCE: 11
acgaggttcc atgtctttca                                              20

<210> SEQ ID NO 12
<211> LENGTH: 31
<212> TYPE: DNA
<213> ORGANISM: Artificial Sequence
<220> FEATURE:
<223> OTHER INFORMATION: Primer OVMUa3

<400> SEQUENCE: 12
taaatagcac agaacgctga ggggagtaag g                                 31

<210> SEQ ID NO 13
<211> LENGTH: 20
<212> TYPE: DNA
<213> ORGANISM: Artificial Sequence
<220> FEATURE:
<223> OTHER INFORMATION: Primer OVMUa4

<400> SEQUENCE: 13
gaagagcttg gtagaagact                                              20

<210> SEQ ID NO 14
<211> LENGTH: 21
<212> TYPE: DNA
<213> ORGANISM: Artificial Sequence
<220> FEATURE:
<223> OTHER INFORMATION: Primer OVMUa5

<400> SEQUENCE: 14
atggaaatat gggtttcctt c                                            21
```

<210> SEQ ID NO 15
<211> LENGTH: 20
<212> TYPE: DNA
<213> ORGANISM: Artificial Sequence
<220> FEATURE:
<223> OTHER INFORMATION: Primer OVMUa6

<400> SEQUENCE: 15
gcagcttatg gctaatcgct                                               20

<210> SEQ ID NO 16
<211> LENGTH: 20
<212> TYPE: DNA
<213> ORGANISM: Artificial Sequence
<220> FEATURE:
<223> OTHER INFORMATION: Primer OVMUa7

<400> SEQUENCE: 16
agtgaccact atctgacctg                                               20

<210> SEQ ID NO 17
<211> LENGTH: 20
<212> TYPE: DNA
<213> ORGANISM: Artificial Sequence
<220> FEATURE:
<223> OTHER INFORMATION: Primer OVMUa8

<400> SEQUENCE: 17
taatcaggaa ggcacacagc                                               20

<210> SEQ ID NO 18
<211> LENGTH: 20
<212> TYPE: DNA
<213> ORGANISM: Artificial Sequence
<220> FEATURE:
<223> OTHER INFORMATION: Primer OVMUP4. 7. 1

<400> SEQUENCE: 18
agatctggag cagcacttgt                                               20

<210> SEQ ID NO 19
<211> LENGTH: 20
<212> TYPE: DNA
<213> ORGANISM: Artificial Sequence
<220> FEATURE:
<223> OTHER INFORMATION: Primer OVMUP4. 7. 2

<400> SEQUENCE: 19
agcatgaagt tcctcaccca                                               20

<210> SEQ ID NO 20
<211> LENGTH: 20
<212> TYPE: DNA
<213> ORGANISM: Artificial Sequence
<220> FEATURE:
<223> OTHER INFORMATION: Primer OVMUP4. 7. 3

<400> SEQUENCE: 20
atggagagga atattccctt                                               20

<210> SEQ ID NO 21
<211> LENGTH: 18
<212> TYPE: DNA
<213> ORGANISM: Artificial Sequence
<220> FEATURE:
<223> OTHER INFORMATION: Primer OVMUP4. 7. 4

<400> SEQUENCE: 21
atttctccag gcgtgtgg                                                                                    18

<210> SEQ ID NO 22
<211> LENGTH: 18
<212> TYPE: DNA
<213> ORGANISM: Artificial Sequence
<220> FEATURE:
<223> OTHER INFORMATION: Primer OVMUP5. 5. 1

<400> SEQUENCE: 22
atttctccag gcgtgtgg                                                                                    18

<210> SEQ ID NO 23
<211> LENGTH: 20
<212> TYPE: DNA
<213> ORGANISM: Artificial Sequence
<220> FEATURE:
<223> OTHER INFORMATION: Primer VMUP5. 5. 2

<400> SEQUENCE: 23
atgcgagtga aggagagttc                                                                                  20

<210> SEQ ID NO 24
<211> LENGTH: 20
<212> TYPE: DNA
<213> ORGANISM: Artificial Sequence
<220> FEATURE:
<223> OTHER INFORMATION: Primer OVMUP5. 5. 3

<400> SEQUENCE: 24
gcagcacgtg taagcttgta                                                                                  20

<210> SEQ ID NO 25
<211> LENGTH: 20
<212> TYPE: DNA
<213> ORGANISM: Artificial Sequence
<220> FEATURE:
<223> OTHER INFORMATION: Primer OVMUP5. 5. 4

<400> SEQUENCE: 25
caaggcaaat tatcagcaga                                                                                  20

<210> SEQ ID NO 26
<211> LENGTH: 9980
<212> TYPE: DNA
<213> ORGANISM: Gallus gallus
<220> FEATURE:
<221> NAME/KEY: 3'UTR
<222> LOCATION: (1)..(255)
<223> OTHER INFORMATION: 3' untranslated region of ovoinhibitor
<221> NAME/KEY: misc_feature
<222> LOCATION: (2761)..(3024)
<223> OTHER INFORMATION: CR1-like element
<221> NAME/KEY: 5'UTR
<222> LOCATION: (9403)..(9920)
<223> OTHER INFORMATION: 5' untranslated region of ovomucoid

<400> SEQUENCE: 26
taggcagagc aataggactc tcaacctcgt gagtatggca gcatgttaac tctgcactgg      60
agtccagcgt gggaaacaat ctgccttgca catgagtctt cgtgggccaa tattccccaa     120
cggttttcct tcagcttgtc ttgtctccta agctctcaaa acacctttttt ggtgaataaa    180 ctcacttggc aacgtttatc tgtcttacct tagtgtcacg tttcatccct attccccttt    240
ctcctcctcc gtgtggtaca cagtggtgca cactggttct tctgttgatg ttctgctctg    300

-continued

```
acagccaatg tgggtaaagt tcttcctgcc acgtgtctgt gttgttttca cttcaaaaag    360
ggccctgggc tccccttgga gctctcaggc atttccttaa tcatcacagt cacgctggca    420
ggattagtcc ctcctaaacc ttagaatgac ctgaacgtgt gctccctctt tgtagtcagt    480
gcagggagac gtttgcctca agatcagggt ccatctcacc cacagggcca ttcccaagat    540
gaggtggatg gtttactctc acaaaaagtt ttcttatgtt tggctagaaa ggagaactca    600
ctgcctacct gtgaattccc ctagtcctgg ttctgctgcc actgctgcct gtgcagcctg    660
tcccatggag ggggcagcaa ctgctgtcac aaaggtgatc ccaccctgtc tccactgaaa    720
tgacctcagt gccacgtgtt gtatagggta aaagtacgg gagggggatg cccggctccc     780
ttcagggttg cagagcagaa gtgtctgtgt atagagtgtg tcttaatcta ttaatgtaac    840
agaacaactt cagtcctagt gttttgtggg ctggaattgc ccatgtggta gggacaggcc    900
tgctaaatca ctgcaatcgc ctatgttctg aaggtatttg ggaaagaaag ggatttgggg    960
gattgcctgt gattggcttt aattgaatgg caaatcacag gaaagcagtt ctgctcaaca   1020
gttggttgtt tcagccaatt cttgcagcca aagagccggg tgcccagcga tataatagtt   1080
gtcacttgtg tctgtatgga tgacagggag gtagggtgac ctgaggacca ccctccagct   1140
tctgctagcg taggtacagt caccacctcc agctccacac gagtcccatc gtggtttacc   1200
aaagaaacac aattatttgg accagtttgg aaagtcaccc gctgaattgt gaggctagat   1260
taatagagct gaagagcaaa tgttcccaac ttgagatac tagttggtat tagtatcaga    1320
ggaacagggc catagcacct ccatgctatt agattccggc tggcatgtac ttttcaagat   1380
gatttgtaac taacaatggc ttattgtgct tgtcttaagt ctgtgtccta atgtaaatgt   1440
tcctttggtt tatataacct tcttgccatt tgctcttcag gtgttcttgc agaacactgg   1500
ctgctttaat ctagtttaac tgttgcttga ttattcttag ggataagatc tgaataaact   1560
ttttgtggct ttggcagact ttagcttggg cttagctccc acattagctt tgctgccttt   1620
ttctgtgaag ctatcaagat cctactcaat gacattagct gggtgcaggt gtaccaaatc   1680
ctgctctgtg aacacattg tctgatgata ccgaaggcaa acgtgaactc aaagaggcac    1740
agagttaaga gaagtctgt gcaattcaga ggaaaagcca aagtggccat tagacacact    1800
ttccatgcag catttgccag taggtttcat ataaaactac aaaatggaat aaaccactac   1860
aaatgggaaa agcctgatac tagaatttaa atattcaccc aggctcaagg ggtgtttcat   1920
ggagtaatat cactctataa aagtagggca gccaattatt cacagacaaa gctttttttt   1980
ttctgtgctg cagtgctgtt tttcggctga tccagggtta cttattgtgg gtctgagagc   2040
tgaatgattt ctccttgtgt catgttggtg aaggagatat ggccagggg agatgagcat    2100
gttcaagagg aaacgttgca ttttggtggc ttgggagaaa ggtagaacga tatcaggtcc   2160
atagtgtcac taagagatct gaaggatggt tttacagaac agttgacttg gctgggtgca   2220
ggcttggctg taaatggatg gaaggatgga cagatgggtg gacagagatt tctgtgcagg   2280
agatcatctc ctgagctcgg tgcttgacag actgcagatc catcccataa ccttctccag   2340
catgagagcg cggggagctt tggtactgtt cagtctgctg cttgttgctt cctgggtgca   2400
cagtggtgat tttcttactc acacagggca aaaacctgag cagcttcaaa gtgaacaggt   2460
tgctctcata ggccattcag ttgtcaagat gaggttttg gtttcttgtt ttgtaaggtg    2520
ggaagaagca ctgaaggatc agttgcgagg gcagggggttt agcactgttc agagaagtct   2580
tattttaact cctctcatga acaaaaagag atgcaggtgc agattctggc aagcatgcag   2640
```

```
tgaaggagaa agccctgaat ttctgatata tgtgcaatgt tgggcaccta acattccccg    2700
ctgaagcaca gcagctccag ctccatgcag tactcacagc tggtgcagcc ctcggctcca    2760
gggtctgagc agtgctggga ctcacgaggt tccatgtctt tcacactgat aatggtccaa    2820
tttctggaat gggtgcccat ccttggaggt ccccaaggcc aggctggctg cgtctccgag    2880
cagcccgatc tggtggtgag tagccagccc atggcaggag ttagagcctg atggtcttta    2940
aggtcccttc caacctaagc catcctacga ttctaggaat catgacttgt gagtgtgtat    3000
tgcagaggca atattttaaa gttataaatg ttttctcccc ttccttgttt gtcaaagtta    3060
tcttgatcgc cttatcaatg cttttggagt ctccagtcat ttttcttaca mcaaaaagag    3120
gaggaagaat gaagagaatc atttaatttc ttgattgaat agtaggattc agaaagctgt    3180
acgtaatgcc gtctctttgt atcgagctgt aaggtttctc atcatttatc agcgtggtac    3240
atatcagcac ttttccatct gatgtggaaa aaaaaatcct tatcatctac agtctctgta    3300
cctaaacatc gctcagactc tttaccaaaa aagctatagg ttttaaaact acatctgctg    3360
ataatttgcc ttgttttagc tcttcttcca tatgctgcgt ttgtgagagg tgcgtggatg    3420
ggcctaaact ctcagctgct gagcttgatg ggtgcttaag aatgaagcac tcactgctga    3480
aactgttttc atttcacagg aatgttttag tggcattgtt tttataacta catattcctc    3540
agataaatga aatccagaaa taattatgca aactcactgc atccgttgca caggtcttta    3600
tctgctagca aaggaaataa tttggggatg gcaaaaacat tccttcagac atctatattt    3660
aaaggaatat aatcctggta cccacccact tcatccctca ttatgttcac actcagagat    3720
actcattctc ttgttgttat catttgatag cgttttcttt ggttctttgc cacgctctgg    3780
gctatggctg cacgctctgc actgatcagc aagtagatgc gagggaagca gcagtgagag    3840
gggctgccct cagctggcac ccagccgctc agcctaggag gggaccttgc ctttccacca    3900
gctgaggtgc agcccctacaa gcttacacgt gctgcgagca ggtgagcaaa gggagtcttc    3960
atggtgtgtt tcttgctgcc cggaagcaaa actttacttt cattcattcc ccttgaagaa    4020
tgaggaatgt ttggaaacgg actgctttac gttcaatttc tctcttccct ttaaggctca    4080
gccaggggcc attgctgagg acggcatcgg ggcccctgg accaaatctg tggcacagat    4140
ggtttcactt acatcagtgg atgtgggatc tgcgcctgta atgtgtcctt ctgaaggaag    4200
gaacgtgcct tccaagtgcc agccccacag cccccagccc ctccctgtgc tgctccaatt    4260
catctcctct tcctccttct cccttttgctg tttgtgctcg ggtagaaatc atgaagattt    4320
agaagagaaa acaaaataac tggagtggaa acccaggtga tgcagttcat tcagctgtca    4380
taggtttgtc gttgctatag gtctgtatca gagatgctar caccactttg ctgtcggtgc    4440
ttaactcggg tgaactctcc ttcactcgca tcatttgcgg gccttattta catccccagc    4500
atccatcacc ctctgggaaa atgggcgcac tggatctcta atggaagact ttccctcttt    4560
cagagcctgt gggatgtgca gtgacaagaa acgtggaggg gctgagcagc agcactgccc    4620
ccagggagca ggagcggatg ccatcggtgg cagcatccca aatgatgtca gcggatgctg    4680
agcaggcagc ggacgaacgg acagaagcga tgcgtacacc ttctgttgac atggtatttg    4740
gcagcgattt aacactcgct tcctagtcct gctattctcc acaggctgca ttcaaatgaa    4800
cgaagggaag ggaggcaaaa agatgcaaaa tccgagacaa gcagcagaaa tatttcttcg    4860
ctacggaagc gtgcgcaaac aaccttctcc aacagcacca aagagcaca gcgtaacctt    4920
tttcaagacc agaaaggaa attcacaaag cctctgtgga taccgcgcg ttcagctctc    4980
ctgatagcag atttcttgtc aggttgcgaa tggggtatgg tgccaggagg tgcagggacc    5040
```

-continued

| | |
|---|---|
| atatgatcat atacagcaca gcagtcattg tgcatgtatt aatatatatt gagtagcagt | 5100 |
| gttactttgc caaagcaata gttcagagat gagtcctgct gcatacctct atcttaaaac | 5160 |
| taacttataa atagtaaaac cttctcagtt cagccacgtg ctcctctctg tcagcaccaa | 5220 |
| tggtgcttcg cctgcaccca gctgcaagga atcagcccgt gatctcatta acactcagct | 5280 |
| ctgcaggata aattagattg ttccactctc ttttgttgtt aattacgacg gaacaattgt | 5340 |
| tcagtgctga tggtcctaat tgtcagctac agaaaacgtc tccatgcagt tccttctgcg | 5400 |
| ccagcaaact gtccaggcta tagcaccgtg atgcatgcta cctctcactc catccttctt | 5460 |
| ctctttccca ccagggagag ctgtgtgttt tcactctcag ccactctgaa caataccaaa | 5520 |
| ctgctacgca ctgcctccct cggaaagaga atccccttgt tgcttttttta tttacaggat | 5580 |
| ccttcttaaa aagcagacca tcattcactg caaacccaga gcttcatgcc tctccttcca | 5640 |
| caaccgaaaa cagccggctt catttgtctt ttttaaatgc tgtttttccag gtgaattttg | 5700 |
| gccagcgtgt tggctgagat ccaggagcac gtgtcagctt tctgctctca ttgctcctgt | 5760 |
| tctgcattgc ctcttttctgg ggtttccaag agggggggag actttgcgcg gggatgagat | 5820 |
| aatgcccctt ttcttagggt ggctgctggg cagcagagtg gctctgggtc actgtggcac | 5880 |
| caatgggagg caccagtggg ggtgtgtttt gtgcagggg gaagcattca cagaatgggg | 5940 |
| ctgatcctga agcttgcagt ccaaggcttt gtctgtgtac ccagtgaaat ccttcctctg | 6000 |
| ttacataaag cccagatagg actcagaaat gtagtcattc cagccccct cttcctcaga | 6060 |
| tctggagcag cacttgtttg cagccagtcc tccccaaaat gcacagacct cgccgagtgg | 6120 |
| agggagatgt aaacagcgaa ggttaattac ctccttgtca aaaacacttt gtggtccata | 6180 |
| gatgtttctg tcaatcttac aaaacagaac cgagaggcag cgagcactga agagcgtgtt | 6240 |
| cccatgctga gttaatgaga cttggcagct cgctgtgcag agatgatccc tgtgcttcat | 6300 |
| gggaggctgt aacctgtctc cccatcgcct tcacaccgca gtgctgtcct ggacacctca | 6360 |
| ccctccataa gctgtaggat gcagctgccc agggatcaag agacttttcc taaggctctt | 6420 |
| aggactcatc tttgccgctc agtagcgtgc agcaattact catcccaact atactgaatg | 6480 |
| ggtttctgcc agctctgctt gtttgtcaat aagcatttct tcattttgcc tctaagtttc | 6540 |
| tctcagcagc accgctctgg gtgacctgag tggccacctg gaacccgagg ggcacagcca | 6600 |
| ccacctccct gttgctgctg ctccagggac tcatgtgctg ctggatgggg ggaagcatga | 6660 |
| agttcctcac ccagacacct gggttgcaat ggctgcagcg tgctcttctt ggtatgcaga | 6720 |
| ttgtttccag ccattacttg tagaaatgtg ctgtggaagc cctttgtatc tctttctgtg | 6780 |
| gcccttcagc aaaagctgtg ggaaagctct gaggctgctt tcttgggtcg tggaggaatt | 6840 |
| gtatgttcct tctttaacaa aaattatcct taggagagag cactgtgcaa gcattgtgca | 6900 |
| cataaaacaa ttcaggttga aagggctctc tggaggtttc cagcctgact actgctcgaa | 6960 |
| gcaaggccag gttcaaagat ggctcaggat gctgtgtgcc ttcctgatta tctgtgccac | 7020 |
| caatggagga gattcacagc cactctgctt cccgtgccac tcatggagag gaatattccc | 7080 |
| ttatattcag atagaatgtt atcctttagc tcagccttcc ctataacccc atgagggagc | 7140 |
| tgcagatccc catactctcc ccttctctgg ggtgaaggcc gtgtccccca gcccccttc | 7200 |
| ccaccctgtg ccctaagcag cccgctggcc tctgctggat gtgtgcctat atgtcaatgc | 7260 |
| ctgtccttgc agtccagcct gggacattta attcatcacc agggtaatgt ggaactgtgt | 7320 |
| catcttcccc tgcagggtac aaagttctgc acggggtcct ttcggttcag gaaaaccttc | 7380 |

```
actggtgcta cctgaatcaa gctctattta ataagttcat aagcacatgg atgtgttttc    7440
ctagagatac gttttaatgg tatcagtgat ttttatttgc tttgttgctt acttcaaaca    7500
gtgcctttgg gcaggaggtg agggacgggt ctgccgttgg ctctgcagtg atttctccag    7560
gcgtgtggct caggtcagat agtggtcact ctgtggccag aagaaggaca aagatggaaa    7620
ttgcagattg agtcacgtta agcaggcatc ttggagtgat ttgaggcagt ttcatgaaag    7680
agctacgacc acttattgtt gttttcccct tttacaacag aagttttcat caaaataacg    7740
tggcaaagcc caggaatgtt tgggaaaagt gtagttaaat gttttgtaat tcatttgtcg    7800
gagtgctacc agctaagaaa aaagtcctac ctttggtatg gtagtcctgc agagaataca    7860
acatcaatat tagtttggaa aaaaacacca ccaccaccag aaactgtaat ggaaaatgta    7920
aaccaagaaa ttccttgggt aagagagaaa ggatgtcgta tactggccaa gtcctgccca    7980
gctgtcagcc tgctgaccct ctgcagttca ggaccatgaa acgtggcact gtaagacgtg    8040
tcccctgcct ttgcttgccc acagatctct gcccttgtgc tgactcctgc acacaagagc    8100
atttccctgt agccaaacag cgattagcca taagctgcac ctgactttga ggattaagag    8160
tttgcaatta agtggattgc agcaggagat cagtggcagg gttgcagatg aaatcctttt    8220
ctaggggtag ctaagggctg agcaacctgt cctacagcac aagccaaacc agccaagggt    8280
tttcctgtgc tgttcacaga ggcagggcca gctggagctg gaggaggttg tgctgggacc    8340
cttctccctg tgctgagaat ggagtgattt ctgggtgctg ttcctgtggc ttgcactgag    8400
cagctcaagg gagatcggtg ctcctcatgc agtgccaaaa ctcgtgtttg atgcagaaag    8460
atggatgtgc acctccctcc tgctaatgca gccgtgagct tatgaaggca atgagccctc    8520
agtgcagcag gagctgtagt gcactcctgt aggtgctagg gaaaatctct ggttcccagg    8580
gatgcattca taagggcaat atatcttgag gctgcgccaa atctttctga aatattcatg    8640
cgtgttccct taatttatag aaacaaacac agcagaataa ttattccaat gcctcccctc    8700
gaaggaaacc catatttcca tgtagaaatg taacctatat acacacagcc atgctgcatc    8760
cttcagaacg tgccagtgct catctcccat ggcaaaatac tacaggtatt ctcactatgt    8820
tggacctgtg aaaggaacca tggtaagaaa cttcggttaa aggtatggct gcaaaactac    8880
tcataccaaa acagcagagc tccagacctc ctcttaggaa agagccactt ggagagggat    8940
ggtgtgaagg ctggaggtga gagacagagc ctgtcccagt tttcctgtct ctattttctg    9000
aaacgtttgc aggaggaaag gacaactgta cttccaggca tagctggtgc cctcacgtaa    9060
ataagttccc cgaacttctg tgtcatttgt tcttaagatg ctttggcaga acactttgag    9120
tcaattcgct taactgtgac taggtctgta ataagtgct ccctgctgat aaggttcaag    9180
tgacattttt agtggtattt gacagcattt accttgcttt caagtcttct accaagctct    9240
tctatactta agcagtgaaa ccgccaagaa acccttcctt ttatcaagct agtgctaaat    9300
accattaact tcataggtta gatacggtgc tgccagcttc acctggcagt ggttggtcag    9360
ttctgctggt gacaaagcct ccctggcctg tgcttttacc tagaggtgaa tatccaagaa    9420
tgcagaactg catggaaagc agagctgcag gcacgatggt gctgagcctt agctgcttcc    9480
tgctgggaga tgtggatgca gagacgaatg aaggacctgt cccttactcc cctcagcatt    9540
ctgtgctatt taggttcta ccagagtcct taagaggttt ttttttttt tggtccaaaa    9600 gtctgtttgt ttggttttga ccactgagag catgtgacac ttgtctcaag ctattaacca    9660
agtgtccagc caaaatcaat tgcctggag acgcagacca ttacctggag gtcaggacct    9720
caataaatat taccagcctc attgtgccgc tgacagattc agctggctgc tccgtgttcc    9780
```

```
agtccaacag ttcggacgcc acgtttgtat atatttgcag gcagcctcgg ggggaccatc    9840
tcaggagcag agcaccggca gccgcctgca gagccgggca gtactctcac catggccatg    9900
gcaggtgtct tcgtgctgtt ctctttcgtg ctttgtggct tcctcccagg tgagtaactc    9960
ccagagtgct gcagaagctt                                                9980

<210> SEQ ID NO 27
<211> LENGTH: 20
<212> TYPE: DNA
<213> ORGANISM: Artificial Sequence
<220> FEATURE:
<223> OTHER INFORMATION: Primer OVMUa9

<400> SEQUENCE: 27
aaatgaagcc ggctgttttc                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer OVINs9

<400> SEQUENCE: 28
ctctcagcca ctctgaacaa                                                  20
```

OVOMUCOID PROMOTER AND METHODS OF USE

GOVERNMENT RIGHTS STATEMENT

This invention was made with government support under a grant from the National Institute of Standards and Technology. Therefore, the U.S. Government may have certain rights in this invention.

FIELD OF THE INVENTION

The present invention relates generally to the identification of an avian ovomucoid gene expression control region. More specifically, the invention relates to recombinant nucleic acids and expression vectors, transfected cells and transgenic animals, especially chickens, that comprise the avian ovomucoid gene expression control region operably linked to a polypeptide-encoding nucleic acid.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology to convert animals into "protein factories" for the production of specific proteins or other substances of pharmaceutical interest (Gordon et al., 1987, *Biotechnology* 5: 1183–1187; Wilmut et al., 1990, *Theriogenology* 33: 113–123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct lined with tubular gland cells. These cells secrete the egg-white proteins, including ovalbumin, ovomucoid, lysozyme, conalbumin and ovomucin, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. As a result, efforts have been made to create transgenic chickens expressing heterologous proteins in the oviduct by means of microinjection of DNA (PCT Publication WO 97/47739).

Chicken oviduct cells, when stimulated by steroid hormones during egg-laying, secrete three principal polypeptides, ovalbumin, ovomucoid and lysozyme (Tsai et al., 1978, *Biochemistry* 17: 5773–5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells (Hynes et al. 1977, *Cell* 11:923–932).

Detailed restriction enzyme analysis of fragments of chicken genomic DNA have shown that the ovomucoid-encoding sequence includes seven intronic sequences (Lindenmaier et al., 1979, *Nuc. Acid Res.* 7;1221–1232; Catterall et al., 1979, *Nature* 278: 323–327; Lai et al., 1979, *Cell* 18:829–842). Short stretches of the 5' flanking region of the ovomucoid gene have been sequenced (Lai et al., 1979, *Cell* 18: 829–842; Genbank Accession No. J00897), but extending only 579 bases upstream of the recognized transcription start site. The 5' flanking region of the ovomucoid gene has been isolated (Catterall et al., 1979, *Nature* 278: 323–327); Lai et al., 1979, *Cell* 18: 829–842) but not generally characterized beyond low-resolution restriction site mapping. Scott et al. identified a CR1-like region within the 10 kb chicken genomic DNA located between the ovoinhibitor-encoding region and the downstream ovomucoid gene (1987, *Biochemistry* 26: 6831–6840). The ovoinhibitor-encoding cDNA and the attached 3'-untranslated region, which extends into the 10 kb ovoinhibitor-ovomucoid region, were also sequenced (Scott et al., 1987, *J. Biol. Chem.* 262: 5899–5907).

The chicken ovomucoid gene, therefore, is highly expressed in the tubular glands of the mature hen oviduct and represents a suitable candidate for an efficient promoter for heterologous protein production in transgenic animals, especially chickens. The regulatory region of the ovomucoid locus extends over a nucleic acid region of at about 10 kb of DNA 5' upstream of the transcription start site, and comprises at least one recognized element, the CR1.

SUMMARY OF THE INVENTION

Briefly described, the present invention relates to a novel isolated avian nucleic acid comprising an avian ovomucoid gene expression control region.

The isolated nucleic acid of the present invention is useful for the expression of an operably linked heterologous nucleic acid insert in a transfected avian cell such as, for example, an oviduct cell.

One aspect of the present invention provides a novel isolated nucleic acid that is located immediately 5' upstream of a transcription start site of the chicken ovomucoid gene locus. The novel isolated avian nucleic acid sequence encoding an ovomucoid gene expression control region comprises at least one avian CR1 repeat element, and a proximal ovomucoid promoter. Interspersed between these constituent elements are stretches of nucleic acid that may serve at least to organize the gene regulatory elements in an ordered array relative to a polypeptide-encoding region. In one embodiment of the present invention the isolated nucleic acid is isolated from a chicken.

The isolated avian ovomucoid promoter region of the present invention is useful for directing expression of a polypeptide-encoding nucleic acid which, in one embodiment, is tissue specific expression. The isolated avian ovomucoid promoter may be operably linked with a selected nucleic acid insert, wherein the nucleic acid insert encodes a polypeptide desired to be expressed in a transfected cell. The nucleic acid insert may be placed in frame with a signal peptide sequence. Translation initiation may start with the signal peptide and continue through the nucleic acid insert, thereby producing an expressed polypeptide having the desired amino acid sequence.

The recombinant DNA of the present invention may further comprise a polyadenylation signal sequence that will allow the transcript directed by the novel ovomucoid gene expression control region to proceed beyond the nucleic acid insert encoding a polypeptide and allow the transcript to further comprise a 3' untranslated region and a polyadenylated tail. Any functional polyadenylation signal sequence, including but not limited to the SV40 polyadenylation signal sequence, bovine growth hormone adenylation sequence or the like, may be linked to the 3' end of the nucleic acid insert.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, ovomucoid, ovomucin, ovotransferrin, and the like in a chicken.

Yet another aspect of the present invention is directed to an expression vector suitable for delivery to a recipient cell for expression of the vector therein. The expression vector of the present invention may comprise an isolated avian ovomucoid gene expression control region operably linked to a nucleic acid insert encoding a polypeptide and, optionally, a polyadenylation signal sequence. The expression vector may further comprise a bacterial plasmid sequence, a viral nucleic acid sequence, or fragments or variants thereof that may allow for replication of the vector in a suitable host.

Another aspect of the present invention is a method of expressing a heterologous polypeptide in a eukaryotic cell by transfecting the cell with a recombinant DNA comprising an avian ovomucoid gene expression control region operably linked to a nucleic acid insert encoding a polypeptide and, optionally, a polyadenylation signal sequence, and culturing the transfected cell in a medium suitable for expression of the heterologous polypeptide under the control of the avian ovomucoid gene expression control region.

Also within the scope of the present invention are recombinant cells, tissues, and animals containing non-naturally occurring recombinant nucleic acid molecules according to the present invention and described above. In one embodiment of the present invention, the transformed cell is a chicken oviduct cell and the nucleic acid insert comprises the chicken ovomucoid gene expression control region, a nucleic acid insert encoding a human interferon α2d and codon optimized for expression in an avian cell, and an SV40 polyadenylation sequence.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 3 shows PCR primers SEQ ID NOS: 1–25 and 27–28 used to PCR amplify and/or sequence the approximately 10 kb nucleic acid region that is 5' upstream of the chicken ovomucoid transcription start site.

FIGS. 4A–D show the nucleic acid sequence SEQ ID NO: 26 of the approximately 10 kb nucleic acid region that is 5' upstream of the chicken ovomucoid transcription start site.

DETAILED DESCRIPTION OF THE PREFERRED EMBODIMENTS

Figure 1:
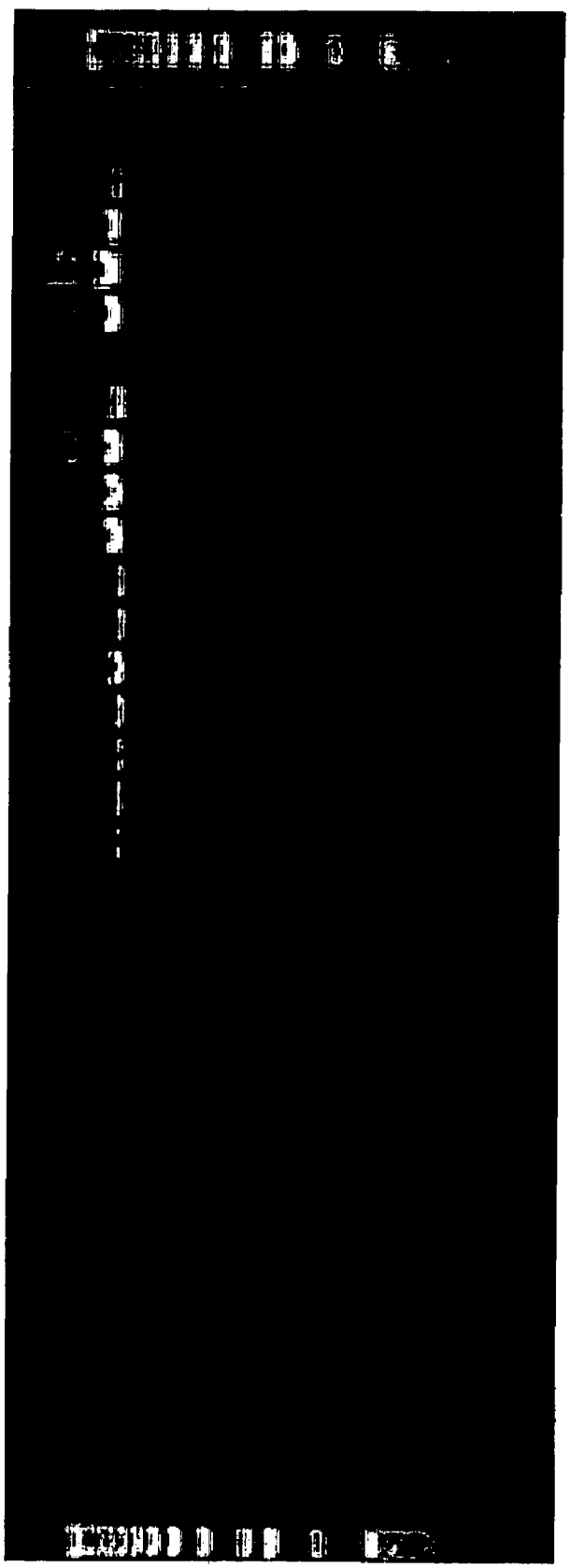
FIG. 1 illustrates an agarose gel analysis of PCR products from PCR amplification of chicken genomic DNA using the primers OVINs2 (SEQ ID NO: 1) and OVMUa2 (SEQ ID NO: 2).

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

This description uses gene nomenclature accepted by the Cucurbit Genetics Cooperative as it appears in the *Cucurbit Genetics Cooperative Report* 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

Definitions

The term "animal" is used herein to include all vertebrate animals, including humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus,* or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes an ovomucoid gene expression control region or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term "significant" as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide, or a portion or fragment thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The term "coding region" as used herein refers to a continuous linear arrangement of nucleotides that may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, chemiluminescent moieties, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of an ovomucoid gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al., 1984, *Anal. Biochem.* 138: 267–284; the contents of which is incorporated herein by reference in its entirety. Protocols for hybridization techniques are well known to those of skill in the art and standard molecular biology manuals may be consulted to select a suitable hybridization protocol without undue experimentation. See, for example, Sambrook et al., 1989, "Molecular Cloning: A Laboratory Manual," 2nd ed., Cold Spring Harbor Press: the contents of which is incorporated herein by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60°

Celsius. Exemplary high stringency conditions include hybridization in 50% formamide, 1 M NaCl, 1% SDS at 37° Celsius, and a wash in 0.1×SSC at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin and Attschul 1990 *Proc. Natl. Acad. Sci.* 87: 2264–2268, modified as in Karlin and Attschul 1993 *Proc. Natl. Acad. Sci.* 90: 5873–5877. Such an algorithm is incorporated into the NBLAST and XBLAST programs of Attschul et al. 1990 *T. Mol. Biol.* Q15: 403–410. BLAST nucleotide searches are performed with the NBLAST program, score=100, wordlength=12, to obtain nucleotide sequences homologous to a nucleic acid molecule of the invention. BLAST protein searches are performed with the XBALST program, score=50, wordlength=3, to obtain amino acid sequences homologous to a reference polypeptide. To obtain gapped alignments for comparison purposes, Gapped BLAST is utilized as described in Attscul et al. 1997 *Nucl. Acids Res.* 25: 3389–3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example, that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the ovomucoid gene expression control region operably linked to a nucleotide sequence coding at least one polypeptide. As used herein, the term "regulatory sequences" includes promoters, enhancers, and other elements that may control gene expression. Standard molecular biology textbooks (for example, Sambrook et al., eds., 1989, "Molecular Cloning: A Laboratory Manual," 2nd ed., Cold Spring Harbor Press) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell including, but not limited to, an avian cell like a chicken male germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to the male germ cells using specific ligands that are recognized by receptors on the cell surface of the germ cell, such as the c-kit ligand or modifications thereof.

Other preferred transfecting agents include, but are not limited to, lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, poly (ethylenimine) (PEI) and the like. These non-viral agents have the advantage that they can facilitate stable integration of xenogeneic DNA sequences into the vertebrate genome, without size restrictions commonly associated with virus-derived transfecting agents.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, a "transgenic animal" is any animal, such as an avian animal including a chicken, in which one or more of the cells of the animal may contain heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide. The terms "chimeric animal" or "mosaic animal" are used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon polypeptide, a human monoclonal antibody, and the like) that is partly or entirely heterologous (i.e., foreign, to the transgenic animal or cell into which it is introduced) or is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene according to the present invention will include one or more transcriptional regulatory sequences, polyadenylation signal sequences, and any other nucleic acids, such as introns, that may be necessary for optimal expression of a selected nucleic acid.

The techniques used to isolate and characterize the nucleic acids and proteins of the present invention are well known to those of skill in the art and standard molecular biology and biochemical manuals may be consulted to select suitable protocols without undue experimentation (see, for example, Sambrook et al., "Molecular Cloning: A Laboratory Manual," 2nd ed., 1989, Cold Spring Harbor Press; the contents of which is incorporated herein by reference in its entirety).

Following longstanding law convention, the terms "a" and "an" as used herein, including the claims, mean "one or more."

Abbreviations

Abbreviations used in the present specification include the following:

aa, amino acid(s); bp, base pair(s); cDNA, DNA complementary to RNA; nt, nucleotide(s); SSC, sodium chloride-sodium citrate; DMSO, dimethyl sulfoxide.

Chicken Ovomucoid Gene Expression Control Region Nucleic Acid Sequences

A series of PCR amplifications of template chicken genomic DNA were used to isolate the gene expression control region of the chicken ovomucoid locus. The region of the chicken genome lying between the 3' end of ovoinhibitor gene and the 5' transcription start site of the ovomucoid gene was PCR amplified using the primers OVINs 2, 5'-TAGGCAGAGCAATAGGACTCTCAACCTCGT-3' (SEQ ID NO: 1) and OVMUa2, 5'-AAGCTTCTGCAGCACTCTGGGAGTTACTCA-3' (SEQ ID NO: 2) as described in detail in Example 1 below and FIG. 1. The approximately 10 kb fragment was blunt-ended and cleaved with the restriction endonuclease Bam HI. The resulting fragments of about 4.7 kb and 5.5 were subcloned into the linearized plasmid vector pBluescript KS II (+/−) (Stratagene, La Jolla, Calif.). Each insert was sequenced using the primers SEQ ID NOS: 5–25 shown in FIGS. 2 and 3 and as described in Example 3 below. The compiled nucleic acid sequence (SEQ ID NOS: 26) of the approximately 10 kb nucleic acid region that is 5' upstream of the chicken ovomucoid transcription start site is shown in FIGS. 4A–D.

SEQ ID NO: 26 includes the ovoinhibitor gene 3' untranslated region described by Scott et al. (J. Biol. Chem. 262: 5899–5909 (1987)) from bases positions 1–255 as shown in FIGS. 4A–D. A CR1-like element (Scott et al., Biochemistry 26: 6831–6840 (1987); Genbank Accession No: M17966) is located at base positions 2761–3024 as shown in FIGS. 4A–D. The region of SEQ ID NO: 26 from base positions 9403–9920, as shown in FIGS. 4A–D, has been described in Genbank Accession No: J00897 and in Lai et al. Cell 18: 829–842 (1979) and includes a portion of the 5' untranslated region of the ovomucoid gene.

It is contemplated that any nucleic acid sequence encoding a polypeptide may be operably linked to the novel isolated avian ovomucoid gene expression control region so as to be expressed in a transfected cell that, in one embodiment of the present invention, may be an avian cell. For example, a plasmid construct contacting the cloned ovomucoid promoter region and a desired polypeptide-encoding nucleic acid sequence may be transfected into cultured quail or chicken oviduct cells, which may then be incubated to synthesize a polypeptide detectable with antibodies directed against the desired polypeptide.

The novel isolated chicken ovomucoid gene expression control region of the present invention comprises the nucleotide elements that are positioned 5' upstream of the transcription start site of the native chicken ovomucoid locus and necessary for the regulated expression of a downstream polypeptide-encoding nucleic acid. It is contemplated that this region includes those transcription control regions regulatable by hormones including, for example, steroid hormones and the like.

One aspect of the present invention, therefore, provides a novel isolated nucleic acid that comprises the nucleotide sequences SEQ ID NO: 26, shown in FIG. 4 (Genbank Accession No. AF 453747), and derivatives and variants thereof located immediately 5' upstream of the transcription start site of the chicken ovomucoid gene locus.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 26, as shown in FIGS. 4A–D, or a variant thereof.

Another aspect of the invention provides nucleic acids that can hybridize under high, medium or low stringency conditions to an isolated nucleic acid comprising a chicken ovomucoid gene expressions control region having all, a derivative of, or a portion of the nucleic acid sequence SEQ ID NO: 26 shown in FIGS. 4A–D and direct expression of a polypeptide coding sequence in an avian oviduct cell. The nucleotide sequence determined from the isolation of the ovomucoid gene expression control region from a chicken (SEQ ID NO: 26) will allow for the generation of probes designed for use in identifying ovomucoid gene expression control regions, or homologs thereof in other avian species.

Fragments of a nucleic acid encoding a portion of the subject ovomucoid gene expression control region are also within the scope of the invention. As used herein, a fragment of the nucleic acid encoding an active portion of an ovomucoid gene expression control region refers to a nucleotide sequence having fewer nucleotides than the nucleotide sequence encoding the entire nucleic acid sequence of the ovomucoid gene expression control region.

In one embodiment of the present invention, the nucleotide sequence of the isolated DNA molecule of the present invention may be used as a probe in nucleic acid hybridization assays for the detection of the ovomucoid gene expression control region. The nucleotide sequence of the present invention may be used in any nucleic acid hybridization assay system known in the art including, but not limited to, Southern blots (Southern, E. M., 1975, *J. Mol. Biol.* 98: 508), Northern blots (Thomas et al., 1980, *Proc. Natl. Acad. Sci.* 77: 5201–05), Colony blots (Grunstein et al., 1975, *Proc. Natl. Acad. Sci.* 72: 3961–65), and the like. Alternately, the isolated DNA molecules of the present invention can be used in a gene amplification detection procedure such as a polymerase chain reaction (Erlich et al., 1991, *Science* 252: 1643–51; the contents of which is incorporated herein by reference in its entirety) or in restriction fragment length polymorphism (RFLP) diagnostic techniques, such as those described by Watson et al. (pps. 519–522 and 545–547 in "Recombinant DNA," $2^{nd}$ edition, 1992, Scientific American Books; the contents of which is incorporated herein by reference).

Nucleotides constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes, and chemiluminescent moieties. Methods useful in selecting appropriate labels and binding protocols for binding the labels to the synthetic nucleotides are well known to those of skill in the art. Standard immunology manuals such as *Promega: Protocol and Applications Guide* (2nd Edition, 1991, Promega Corp., Madison, Wis.; the contents of which is incorporated herein in its entirety) may be consulted to select an appropriate labeling protocol without undue experimentation.

In another embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived ovomucoid gene expression control region-encoding nucleic acid molecule as depicted in SEQ ID NO: 26.

In another embodiment of the present invention, an avian ovomucoid gene expression control region gene or nucleic acid molecule can be an allelic variant of SEQ ID NO: 26.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill. Additionally, such nucleotides, probes, and primers can be purchased commercially from a variety of sources (e.g., Sigma Genosys, The Woodlands, Tex. or The Great American Gene Co., Ramona, Calif.).

The nucleic acid sequence of a chicken ovomucoid gene expression control region nucleic acid molecule (SEQ ID NO: 26) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain ovomucoid gene expression control region nucleic acid homologs in other species including avian species such as, but not limited to, turkey, duck, goose, quail, pheasant, parrot, finch, ratites including ostrich, emu and cassowary and, (d) to obtain isolated nucleic acids capable of hybridizing to an avian ovomucoid gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken ovomucoid gene expression control region include, but are not limited to, GenBank and the mammalian Gene Index database of The Institute of Genomics Research (TIGR).

Codon-optimized Proteins

Another aspect of the present invention provides a recombinant DNA molecule comprising the novel isolated avian ovomucoid gene expression control region of the present invention operably linked to a selected polypeptide-encoding nucleic acid insert, which may express the nucleic acid insert when transfected to a suitable host cell such as an avian cell. In one embodiment of the present invention, the nucleic acid insert is placed in frame with a signal peptide sequence, whereby translation initiation from the transcript starts with the signal peptide and continues through the nucleic acid insert, thereby producing an expressed polypeptide having the desired amino acid sequence.

It is anticipated that the recombinant DNA may further comprise a polyadenylation signal sequence that will allow the transcript directed by the novel ovomucoid gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including, but not limited to, the SV40 polyadenylation signal sequence, the bovine growth hormone adenylation sequence, or the like, or derivatives thereof.

Another aspect of the present invention is to provide nucleic acid sequences of a protein optimized for expression in avian cells, and derivatives and fragments thereof.

One embodiment of the present invention is a recombinant DNA molecule comprising the isolated avian ovomucoid gene expression control region of the present invention, operably linked to a nucleic acid insert encoding a polypeptide, and a polyadenylation signal sequence optionally operably linked thereto. It is contemplated that when the recombinant DNA is to be delivered to a recipient cell for expression therein. The sequence of the nucleic acid sequence may be modified so that the codons are optimized for the codon usage of the recipient species. For example, if the recombinant DNA is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, ovomucoid, lysozyme, ovomucin, ovotransferrin and the like from a chicken.

In one embodiment of the recombinant DNA of the present invention, for example, the nucleic acid insert may encode the human interferon α2b polypeptide. Optimization of the sequence for codon usage elevates the level of translation in avian eggs. The sequence of the optimized human interferon sequence is disclosed in U.S. patent application Ser. No. 09/173,864, now U.S. Pat. No. 6,730,822, which is incorporated herein by reference in its entirety.

In yet another embodiment of the present invention, the recombinant DNA comprises the isolated avian ovomucoid gene expression control region operably linked to a nucleic acid encoding a human interferon α2b and the SV40 polyadenylation sequence.

The protein of the present invention may be produced in purified form by any known conventional technique. For example, chicken cells may be homogenized and centrifuged and the supernatant then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Recombinant Nucleic Acids, and Expression thereof, Under the Control of an Avian Ovomucoid Promoter Another potentially useful application of the novel isolated ovomucoid gene expression control region of the present invention is the possibility of increasing the amount of a heterologous protein present in an animal, especially a chicken, by gene transfer. In most instances, a heterologous polypeptide-encoding nucleic acid insert transferred into the recipient animal host will be operably linked with the ovomucoid gene expression control region to allow the cell to initiate and continue production of the genetic product protein. A recombinant DNA molecule of the present invention can be transferred into the extra-chromosomal or genomic DNA of the host.

The recombinant DNA nucleic acid molecules of the present invention can be delivered to cells using conventional recombinant DNA technology. The recombinant DNA molecule may be inserted into a cell to which the recombinant DNA molecule is heterologous (i.e. not normally present). Alternatively, as described more fully below, the recombinant DNA molecule may be introduced into cells which normally contain the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated ovomucoid gene expression control region.

U.S. Pat. No. 4,237,224 to Cohen and Bover, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for expression of the vector therein. It is contemplated to be within the scope of the present invention for the expression vector to comprise an isolated avian ovomucoid gene expression control region operably linked to a nucleic acid insert encoding a polypeptide and, optionally, a polyadenylation signal sequence. The expression vector of the present invention may further comprise a bacterial plasmid sequence, a viral nucleic acid sequence, and the like, or fragments or variants thereof, that allow for replication of the vector in a suitable host.

The novel isolated avian ovomucoid gene expression control region of the present invention (SEQ ID NO: 26) and a polypeptide-encoding nucleic acid sequence operably linked thereto and, optionally, a polyadenylation signal sequence may be introduced into a virus including, but not limited to, a vaccinia virus, a retrovirus, a poxvirus, and the like. Methods for making a viral recombinant vector useful for expressing a protein under the control of the ovomucoid promoter are analogous to the methods disclosed in U.S. Pat. Nos. 4,603,112; 4,769,330; 5,174,993; 5,505,941; 5,338,683; 5,494,807; 4,722,848; Paoletti E., 1996, *Proc. Natl. Acad. Sci.,* 93: 11349–11353; Moss, B., 1996, *Proc. Natl. Acad. Sci.* 93: 11341–11348; Roizman, 1996, *Proc. Natl. Acad. Sci.* 93: 11307–11302; Frolov et al., 1996, *Proc. Natl. Acad. Sci.* 93: 11371–11377; Grunhaus et al., 1993, *Seminars in Virology* 3: 237–252 and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif.; hereby incorporated by reference), pQE, pIH821, pGEX, pET series (see Studier, F. W. et. al., 1990, "Use of T7 RNA Polymerase to Direct Expression of Cloned Genes," *Gene Expression Technology,* vol. 185; hereby incorporated herein by reference in its entirety) and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al. (1989, "Molecular Cloning: A Laboratory Manual," 2nd ed., Cold Spring Harbor Press; the contents of which is incorporated herein by reference in its entirety).

A variety of host-vector systems may be utilized to express the protein-encoding sequence(s). Primarily, the vector system must be compatible with the host cell used. The use of eukaryotic recipient host cells permits partial or complete post-translational modification such as, but not only, glycosylation and/or the formation of the relevant inter- or intra-chain disulfide bonds. Host-vector systems include, but are not limited to, the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, retroviruses, and the like); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Once the novel isolated ovomucoid gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection including pronuclear, nuclear transfer, and the like.

Another aspect of the present invention, therefore, is a method of expressing a heterologous polypeptide in a eukaryotic cell by transfecting the cell with a recombinant DNA comprising an avian ovomucoid gene expression control region operably linked to a nucleic acid insert encoding a polypeptide and, optionally, a polyadenylation signal sequence, and culturing the transfected cell in a medium suitable for expression of the heterologous polypeptide under the control of the avian ovomucoid gene expression control region.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken ovomucoid gene expression control region, a nucleic acid insert encoding a human interferon α2d and codon optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated that the scope of the present invention encompasses a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the present invention contemplates the avian to be a chicken and the heterologous protein produced under the transcriptional control of the isolated avian ovomucoid gene expression control region produced in the white of an egg.

Viral Vector Cell Transformation

An exemplary approach for the in vivo introduction of a nucleic acid encoding the novel isolated ovomucoid gene expression control region into a cell is by use of a viral vector containing nucleic acid, e.g., a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid encoding an ovomucoid gene expression control region, thereby rendering the retrovirus replication defective. Protocols for producing recombinant retroviruses and for infecting cells in vitro or in vivo with such viruses can be found in Ausubel et al., eds, "Current Protocols in Molecular Biology," (1989, Greene Publishing Associates, Sections 9.10–9.14) and other standard laboratory manuals and disclosed in PCT Application No. 99/19472 to Ivarie et al., among others. Examples of suitable retroviruses include pLJ, pZIP, pWE, pEM, avian leucosis virus (ALV), and the like. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., 1989, *Proc. Natl. Acad. Sci.* 86: 9079–9083; Julan et al., 1992, *J. Gen. Virol.* 73: 3251–3255 and Goud et al., 1983, *Virology* 163: 251–254) or coupling cell surface ligands to the viral env proteins (Neda et al., 1991, *J. Biol. Chem.* 266: 14143–14146) (all of which are incorporated herein by reference in their entireties). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, *BioTechniques* 6: 616; Rosenfeld et al., 1991, *Science* 252: 43 1434; and Rosenfeld et al., 1992, *Cell* 68: 143–155, all of which are incorporated herein by reference in their entireties). Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., 1979, *Cell* 16:683; Berkner et al., supra; and Graham et al., 1991, pp. 109–127 in "Methods in Molecular Biology," vol. 7, E. J. Murray, ed., Humana, Clifton, N.J., all of which are incorporated herein by reference in their entireties. Expression of an inserted gene such as, for example, encoding the human interferon α2b, can be under control of the exogenously added ovomucoid gene expression control region sequences.

Yet another viral vector system useful for delivery of, for example, the subject avian ovomucoid gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector, such as that described in Tratschin et al., 1985, *Mol. Cell. Biol.* 5: 3251–3260, can be used to introduce DNA into cells. A variety of nucleic acids have been introduced into different cell types using AAV vectors (see, for example, Hermonat et al., 1984, *Proc. Natl. Acad. Sci.* 81: 6466–6470; Tratschin et al., 1985, *Mol. Cell. Biol.* 4: 2072–2081; Wondisford et al., 1988, *Mol. Endocrinol.* 2: 32–39; Tratschin et al., 1984, *J. Virol.* 51: 611–619; and Flotte et al., 1993, *J. Biol. Chem.* 268: 3781–3790; all of which are incorporated herein by reference in their entireties).

Non-viral Expression Vectors

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject ovomucoid gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated ovomucoid gene expression control region of the present invention can be entrapped in liposomes bearing positive charges on their surface (e.g., lipofectins) and (optionally) which are tagged with antibodies against cell surface antigens of the target tissue (PCT publication WO91/06309; the content of which is incorporated herein by reference in its entirety).

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180; the contents of which are incorporated herein by reference in their entireties). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., 1993, *Science* 260–926; Wagner et al., 1992, *Proc. Natl. Acad. Sci.* 89: 7934; and Christiano et al., 1993, *Proc. Natl. Acad. Sci.* 90: 2122; the contents of which are incorporated herein by reference in their entireties). It is further contemplated that a recombinant DNA molecule comprising the novel isolated ovomucoid gene expression control region of the present invention may be delivered to a recipient host cell by other non-viral methods including by gene gun, microinjection, sperm-mediated transfer, or the like.

Transgenic Animals

Another aspect of the present invention concerns transgenic animals, such as chickens, that contain a transgene comprising the novel isolated ovomucoid gene expression control region of the present invention and that preferably (though optionally) express a heterologous gene in one or more cells in the animal. Suitable methods for the generation of transgenic avians having heterologous DNA incorporated therein are described, for example, in PCT Published Application No. WO 99/19472 to Ivarie et al., and incorporated herein by reference in its entirety.

In various embodiments of the present invention, the expression of the transgene may be restricted to specific subsets of cells, tissues or developmental stages utilizing, for example, cis-acting sequences acting on the ovomucoid gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous polypeptide and operably linked to the novel isolated avian ovomucoid gene expression control region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian ovomucoid gene expression control region comprising the nucleic acid sequence in SEQ ID NO: 26, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding a polypeptide has a codon complement optimized for protein expression in an avian.

In another embodiment of the transgenic avian of the present invention, the transgenic avian produces the heterologous polypeptide in the serum or in the white of an egg.

In another embodiment of the transgenic avian of the present invention, the transgenic avian produces the heterologous polypeptide in an egg white.

The present invention is further illustrated by the following examples, which are provided by way of illustration and should not be construed as limiting. The contents of all references, published patents and patents cited throughout the present application are hereby incorporated by reference in their entireties.

EXAMPLE 1

PCR Amplification of Ovomucoid Promoter

Sense primer OVINs2, 5'-TAGGCAGAGCAATAGGACTCTCAACCTCGT-3' (SEQ ID NO: 1) and the antisense primer, OVMUa2, 5'-AAGCTTCTGCAGCACTCTGGGAGTTACTCA-3' (SEQ ID NO: 2) were designed according to the sequences of chick ovoinhibitor exon 16 (Genbank Accession No: M16141) and a fragment of the chick ovomucoid promoter region (Genbank Accession No: J00897) respectively. The template DNA for PCR amplification of the ovomucoid promoter region was prepared from blood obtained from a white leghorn chick.

Figure 2:
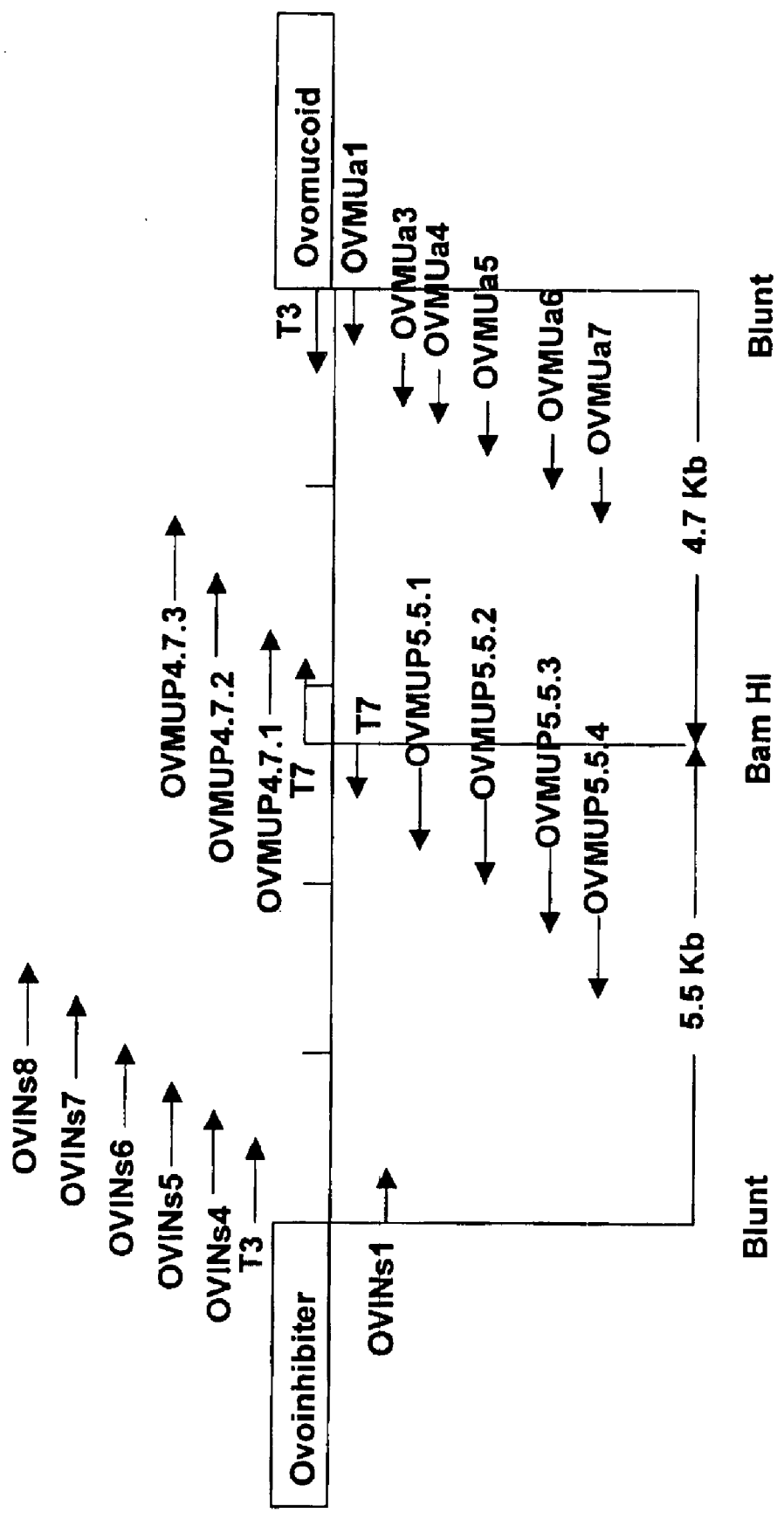
FIG. 2 illustrates the approximately 10 kb nucleic acid region that is 5' upstream of the chicken ovomucoid transcription start site, and the positions and orientations of primers used to sequence this region.

A series of different PCR conditions were carried out to optimize synthesis of the approximately 10.0 kb product, the results of which are shown in FIG. 2. In these tests, the template DNA concentrations were 500 ng, 100 ng, 50 ng, or 10 ng. Two sets of primers, OVINs1 (SEQ ID NO: 3) and OVMUa1 (SEQ ID NO: 4), or OVINs2 (SEQ ID NO: 1) and OVMUa2 (SEQ ID NO: 2) shown in FIG. 3, three $Mg^{++}$ concentrations (1.0 mM, 1.5 mM and 2.0 mM) and annealing temperatures from 50° C. to 70° C. were used.

The results of the tests were as shown in FIG. 2. As shown in lanes 1 through 8, test reactions using 500 ng DNA template; OVINs1 (SEQ ID NO: 3) and OVMUa1 (SEQ ID NO: 4) primers; 60 mM Tris-$SO_4$, pH 9.1; 18 mM $(NH_4)_2SO_4$; 1.0 mM $Mg^{2+}$; and annealing temperatures between 50° C. to 58° C. gave no specific DNA product. Also, as shown in lanes 17 through 24 of FIG. 2, test reactions using 100 ng DNA template; OVINs1 and OVMUa1 primers; 60 mM Tris-$SO_4$, pH 9.1; 18 mM $(NH_4)_2SO_4$; 1.0 mM $Mg^{2+}$; and annealing temperatures between 50° C. to 58° C. did not result in the production of specific bands. However, as shown in lanes 9 through 16 of FIG. 2, test reactions using 500 ng DNA template; OVINs2 (SEQ ID NO: 1) and OVMUa2 (SEQ ID NO: 2) primers; 60 mM Tris-$SO_4$, pH 9.1; 18 mM $(NH_4)_2SO_4$; 2 mM $Mg^{2+}$; and annealing temperatures between 60° C. to 68° C. produce a band of the desired length of approximately 10 kb. As shown in lanes 25 through 32, reaction conditions containing 100 ng DNA template; OVINs2 (SEQ ID NO: 1) and OVMUa2 (SEQ ID NO: 2) primers; 60 mM Tris-$SO_4$, pH 9.1; 18 mM $(NH_4)_2SO_4$; 2 mM $Mg^{2+}$; and annealing temperatures between about 60° C. to about 68° C. gave an increased yield of the desired product.

An approximately 10 kb product was, therefore, detected when the following conditions were used: the optimum DNA template concentration was between about 50 ng to 500 ng; the primers were OVINs2 (SEQ ID NO: 1) and OVMUa2 (SEQ ID NO: 2); the $Mg^{2+}$ concentration was 2 mM; and the annealing temperature was at or between about 60° C. to about 68° C. Each 50 μl PCR reaction consisted of 50 ng or 100 ng of template DNA, 0.1 μg of each primer, 5 μl buffer B (Elongase Enzyme Mix, Gibco BRL), 1 ml of 10 μM dNTP solution, and distilled deionized water. The PCR protocol comprised one cycle at 94° C. for 30 secs; thirty cycles, each at 94° C. for 30 secs, 60° C. for 30 secs, and 68° C. for 10 mins; one cycle at 68° C. for 10 mins than 35° C. for 30 mins; with a final hold at 4° C. Resulting PCR products were examined using 0.65% agarose gel analysis.

EXAMPLE 2

Cloning of PCR Products

The PCR products were purified by standard methods. Briefly, phenol:chloroform:isoamyl alcohol (24:25:1) extraction and chloroform extraction were performed, followed by precipitation of the DNA by adding 3M sodium acetate, pH 5.2, at a final concentration of 0.3M together with 2.5 volumes of 100% ethanol. The DNA pellet was dried and dissolved in deionized water and then sequenced on a ABI3700 automatic sequencer (Applied Biosystems) using the primers OVINs2 (SEQ ID NO: 1) and OVMUa2 (SEQ ID NO: 2) to confirm the identity of each PCR product. After the identities were confirmed, the approximately 10 kb PCR product was treated with T4 polynucleotide kinase to add a phosphate to the 5' end. Mung bean nuclease was used to remove overhanging adenines from the ends of the PCR products, thereby producing a blunt end. The PCR product was purified by phenol:chloroform:isoamyl alcohol extraction and chloroform extraction and precipitated as described above. The 10 kb product was then cleaved using Bam HI to give two fragments of about 4.7 and about 5.5 kb, respectively.

The vector plasmid pBluescript II KS (+/−) was cut by Bam HI and Eco RV and treated with calf intestinal alkaline phosphatase. The DNA fragments to be ligated into the vector were analyzed by agarose gel electrophoresis and purified from agarose gel slices using a NucleoTrap Nucleic Acid Purification Kit (Clontech). The 4.7 kb and 5.5 kb fragments were inserted into the Bam HI/Eco RV-treated pBluescript to give the pBS-OVMUP4.7 and pBS-OVMUP5.5 constructs, respectively.

Positive clones were screened by Xba I/Xho I digestion. Clone pBS-OVMUP4.7 gave fragments of about 4.7 kb and 2.96 kb. Clone pBS-OVMUP5.5 gave fragments of about 5.5 kb and 2.96 kb. The presence of the 4.7 kb in putatively positive clones was further confirmed using Xba I/Hind III digestion, giving three fragments of 0.5 kb, 4.2 kb, and 2.9 kb. Putative positive clones with an insert of about 5.5 kb insert were further confirmed by Xba I/Kpn I digestion, giving three fragments of 2 kb, 3.5 kb and 2.96 kb.

A construct containing the entire 10 kb PCR product cloned into the pBluescript KS II (+/−) vector was made by taking a 4.7 kb Bam HI/Xho I fragment from the pBS-OVMUP4.7 plasmid and inserting it into the Bam HI/Xba I cleaved sites of pBS-OVMUP5.5. The Xho I and Xba I cut ends were blunt-ended by treating the digested fragments with Klenow enzyme and dNTPs at 25° C. for 15 mins before the digestion with Bam HI.

EXAMPLE 3

Sequencing

Plasmids pBS-OVMUP4.7 and pBS-OVMUP5.5 were sequenced from both ends of each insert as shown in FIG. 1. The initial primers were T7 and T3 having the nucleic acid sequences 5'-TAATACGACTCACTATAGGG-3' (SEQ ID NO: 5) and 5'-ATTAACCCTCACTAAAGGGA-3' (SEQ ID NO: 6), respectively. Subsequent primers (SEQ ID NOS: 7–25), as shown in FIG. 3, were designed according to the sequence results as they became available. The approximately 10 kb sequence was edited and assembled using ContigExpress software of the Vector NTI Suite, version 6.0 (InforMax, Inc.). The region of the approximately 10 kb PCR product, described in Example 1 above, encompassing the Bam HI junction was sequenced using OVMUa9 (SEQ ID NO 27) and OVINs9 (SEQ ID NO 28) primers (shown in FIG. 3).

Each sequence chromatogram was visually checked for sequence for accuracy and to locate base ambiguities. Regions containing ambiguous bases were re-sequenced with the same primer or, it still ambiguous, with a new primer designed to sequence the complementary strand. Sequencing of the original 10 kb PCR fragment using primers OVMUa9 (SEQ ID NO 27) and OVINs9 (SEQ ID NO 28) showed that the subcloned inserts of the plasmids pBS-OVMUP4.7 and pBS-OVMUP5.5 included all of the nucleic acid sequence of the parent fragment. No intervening Bam HI-Bam HI fragments were included in the final sequence SEQ ID NO: 26. SEQ ID NO: 26, shown in FIGS. 4A–D, is the sequence of the region lying between the 3' end of the ovoinhibitor gene and the transcription start site of the ovomucoid-encoding region.

EXAMPLE 4

Expression in Transfected Cultured Avian Oviduct Cells of Human Interferon α2b Regulated by the 12 kb Ovomucoid Promoter The oviduct of a Japanese quail (*Coturnix coturnix japonica*) will be removed and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and triturating for 30 minutes at 37° C. The cell suspension will then be filtered through sterile surgical gauze, washed three times with F-12 medium (Life Technologies, Grand Island, N.Y.) by centrifugation at 200× g, and resuspended in OPTIMEM™ (Life Technologies) such that the $OD_{600}$ will be approximately 2. 300 μl of the cell suspension will be plated in each of a 24-well dish. For each transfection, 2.5 μl of DMRIE-C liposomes (Life Technologies) and 1 μg of DNA, comprising the ovomucoid promoter region (SEQ ID NO: 26) and a chicken optimized human interferon α-2b encoding sequence (as disclosed in U.S. patent application Ser. No. 09/173,864, incorporated herein by reference in its entirety, will be preincubated for 15 minutes at room temperature in 100 μl of OPTIMEM™, and then added to the oviduct cells. Cells with DNA/liposomes will be incubated for about 5 hours at 37° C. in 5% $CO_2$. Next, 0.75 ml of DMEM (Life Technologies), supplemented with 15% fetal bovine serum (FBS) (Atlanta Biologicals, Atlanta, Ga.), 2×penicillin/streptomycin (Life Technologies), $10^{-6}$ M insulin (Sigma), $10^{-8}$ M α-estradiol (Sigma), and $10^{-7}$ M corticosterone (Sigma) will be added to each well, and incubation was continued for 72 hours. Medium will then be harvested and centrifuged at 110×g for 5 minutes. The supernatant will be analyzed by ELISA for human interferon α2b content.

The human interferon α2b contents of medium derived from cultured oviduct cells transfected with a plasmid having human interferon α2b cDNA operably linked to the chicken ovomucoid promoter region (SEQ ID NO: 26) will be determined.

What is claimed is:

1. An isolated nucleic acid comprising an avian ovomucoid gene expression controlling region comprising at least one of a nucleotide sequence at least 95% identical to the sequence of SEQ ID NO: 26 or its complement.

2. The isolated nucleic acid of claim 1 wherein the nucleotide sequence is at least 99% identical to the sequence of SEQ ID NO: 26.

3. The isolated nucleic acid of claim 1 wherein the nucleotide sequence comprises the sequence of SEQ ID NO: 26.

4. A recombinant DNA molecule comprising an isolated avian ovomucoid gene expression controlling region at least 95% identical to the sequence of SEQ ID NO: 26 operably linked to a nucleic acid insert encoding a polypeptide.

5. The recombinant DNA molecule of claim 4 wherein the gene expression control region is at least 99% identical to the sequence of SEQ ID NO: 26.

6. The isolated recombinant DNA molecule of claim 4 wherein the gene expression control region comprises the sequence of SEQ ID NO2 26.

7. The recombinant DNA molecule of claim 4 comprising a polyadenylation signal sequence.

8. The recombinant DNA molecule of claim 7 wherein the polyadenylation signal sequence is an SV40 virus polyadenylation sequence.

9. The recombinant DNA molecule of claim 4 wherein the nucleic acid insert encoding a polypeptide comprises condons optimized for protein expression in an avian.

10. The recombinant DNA molecule of claim 4 wherein the nucleic acid insert encodes an interferon α2b polypeptide.

11. The recombinant DNA molecule of claim 4 further comprising an origin of replication selected from the group consisting of a bacterial origin of replication and a viral origin of replication.

12. The recombinant DNA molecule of claim 4 wherein the recombinant DNA molecule is a plasmid.

13. The recombinant DNA molecule of claim 4 wherein the recombinant DNA molecule is a virus.

14. An expression vector that integrates into a host cell comprising an avian ovomucoid gene expression controlling region a nucleotide sequence at least 95% identical to the sequence of SEQ ID NO: 26 operably linked to a nucleic acid encoding a polypeptide wherein the gene expression controlling region directs production of a transcript.

15. The expression vector of claim 14 wherein the nucleotide sequence is at least 99% identical to the sequence of SEQ ID NO: 26.

16. The expression vector of claim 14 wherein the nucleotide sequence comprises the sequence of SEQ ID NO: 26.

17. The expression vector of claim 14 comprising a coding sequence for a polyadenylation signal sequence.

18. The expression vector of claim 17 wherein the polyadenylation signal sequence is an SV40 virus polyadenylation signal sequence.

19. The expression vector of claim 14 wherein the nucleic acid encoding a polypeptide comprises codons optimized for protein expression in an avian.

20. The expression vector of claim 14 wherein the nucleic acid encodes an interferon α2b polypeptide.

21. The expression vector of claim 14 wherein the expression vector is selected from the group consisting of a plasmid and a virus.

22. An isolated eukaryotic cell transformed with the expression vector of claim 14 or a progeny of the cell wherein the cell or progeny thereof is a cultured cell expressing a heterologous polypeptide.

23. The isolated eukaryotic cell of claim 22 wherein the cell is an avian cell.

24. The isolated eukaryotic cell of claim 22 wherein the cell is a chicken cell.

25. The isolated eukaryotic cell of claim 22 wherein the cell is a chicken oviduct cell.

26. The isolated eukaryotic cell of claim 22 wherein the cell is a quail oviduct cell.

27. The isolated eukaryotic cell of claim 22 wherein the nucleic acid encoding a polypeptide comprises codons optimized for protein expressions in an avian.

28. The isolated eukaryotic cell of claim 22 wherein the nucleic acid encoding a polypeptide encodes an interferon α2b polypeptide.

29. A method of expressing a heterologous polypeptide in a host cell comprising:
   transfecting a eukaryotic cell with a recombinant DNA molecule comprising an avian ovomucoid gene expression controlling region comprising a nucleotide sequence at least 95% identical to the sequence of SEQ ID NO: 26 operably linked to a polypeptide encoding a polypeptide thereby making a transfected cell and
   culturing the transfecting cell in a medium suitable for expression of a heterologous polypeptide under the control of an avian ovomucoid gene expression controlling region encoded by the recombinant DNA molecule, thereby expressing a heterologous polypeptide in a host cell.

30. The method of claim 29 wherein the nucleotide sequence is at least 99% identical to the sequence of SEQ ID NO: 26.

31. The method of claim 29 wherein the nucleotide sequence comprises the sequence of SEQ ID NO: 26.

32. The method of claim 29 wherein the eukaryotic cell is isolated from an avian.

33. The method of claim 29 wherein the eukaryotic cell is isolated from a chicken.

34. The method of claim 29 wherein the eukaryotic cell is a chicken oviduct cell.

35. The method of claim 29 wherein the eukaryotic cell is a quail oviduct cell.

36. The method of claim 29 wherein the nucleic acid encoding a polypeptide comprises condons optimized for protein expression in an avian.

37. The method of claim 29 wherein the nucleic acid encoding a polypeptide encodes an interferon α2b polypeptide.

* * * * *